US012653466B2

(12) United States Patent
Risher-Kelly et al.

(10) Patent No.: US 12,653,466 B2
(45) Date of Patent: Jun. 16, 2026

(54) PATIENT MONITORING SYSTEM HAVING A MODULAR CONFIGURATION INCLUDING MULTIPLE MONITORS

(71) Applicant: Drägerwerk AG & Co. KGaA, Lübeck (DE)

(72) Inventors: Clifford M. Risher-Kelly, Wells, ME (US); John C. Magill, Woburn, MA (US); Zachary Kurt Hennings, Concord, NH (US); Thomas Swyst, Arlington, MA (US); Christopher Aiston, Mont Vernon, NH (US); Andrew T. Provencher, Lowell, MA (US); Peter A. Lund, Nashua, NH (US); Joseph Fallon, Brunswick, ME (US); Ricardo Luis Fernandez, Beverly, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 367 days.

(21) Appl. No.: 18/270,091

(22) PCT Filed: Aug. 27, 2021

(86) PCT No.: PCT/EP2021/073785
§ 371 (c)(1),
(2) Date: Jun. 28, 2023

(87) PCT Pub. No.: WO2022/144098
PCT Pub. Date: Jul. 7, 2022

(65) Prior Publication Data
US 2024/0065641 A1     Feb. 29, 2024

Related U.S. Application Data

(60) Provisional application No. 63/131,601, filed on Dec. 29, 2020.

(51) Int. Cl.
*A61B 5/00*          (2006.01)

(52) U.S. Cl.
CPC ...... *A61B 5/7445* (2013.01); *A61B 2560/045* (2013.01); *A61B 2560/0456* (2013.01)

(58) Field of Classification Search
CPC ............ A61B 5/7445; A61B 2560/045; A61B 2560/0456; A61B 5/0205; A61B 5/742; H04M 1/72409; G06F 1/1632
See application file for complete search history.

(56) References Cited

U.S. PATENT DOCUMENTS 9,153,112 B1 * 10/2015 Kiani ..................... G08B 13/22
2019/0183435 A1     6/2019 Eslava et al.

FOREIGN PATENT DOCUMENTS

WO     WO-2020136271 A1 *  7/2020  ............. H01R 13/64

OTHER PUBLICATIONS

European Patent Office, The International Search Report and the Written Opinion of the International Searching Authority, Dec. 7, 2021, for International Application No. PCT/EP2021/073785.

* cited by examiner

*Primary Examiner* — Rex R Holmes
(74) *Attorney, Agent, or Firm* — Nolte Lackenbach Siegel

(57)          ABSTRACT

A monitor mount is configured to detachably secure a first monitor and/or a second monitor individually or concurrently. The first monitor is further configured to be detachably secured to the second monitor independently from either monitor being secured to the monitor mount. The second monitor includes a mounting area in which the first monitor is mounted, and the first monitor and the second monitor are configured such that the first monitor is interchangeably insertable into the mounting area from a first lateral direction and a second lateral direction that is opposite to the first lateral direction. Accordingly, the second monitor includes a dual-entry feature that enables the first monitor to be inserted from either lateral side of the second monitor.

20 Claims, 22 Drawing Sheets

200

501

140

502

221

120

160

501          140

502

140

241

1116b

1118b

1114b

140

241

1116b

1114b

1118b

1122

1120

PATIENT MONITORING SYSTEM HAVING A MODULAR CONFIGURATION INCLUDING MULTIPLE MONITORS

CROSS REFERENCE TO RELATED APPLICATIONS

This application claims priority to PCT application PCT/EP2021/073785 Filed on Aug. 27, 2021 which claims the benefit of U.S. Provisional Patent application 63/131,601 filed on Dec. 29, 2020, both of which are herein incorporated by reference in their entirety for all purposes.

FIELD

The present disclosure generally relates to a patient monitor system having a mount, a smaller monitor, and a larger monitor that is adapted to removably receive the smaller monitor, with the smaller monitor and/or the larger monitor configured to be removably attached to the mount alone or in combination, and to provide for data and power transfer between the monitors and the mount.

BACKGROUND

Monitors that include electronic visual displays are utilized in a large number of applications within a wide variety of industries including, for example, the healthcare industry, the military, and the oil and gas industry. Many of the applications within such industries require such monitors to, at times, be portable, and, at other times, be stationary. For example, in the healthcare industry, when not being used in transport of a patient or when a patient is ambulatory, monitors can be connected to a monitor mount. Such monitor mounts can provide a variety of functions including providing physical support, a power source, and a conduit to one or more computer networks.

One type of monitor is a patient monitor which is used by healthcare facilities to monitor and display information about a patient, such as vital signs, status of connected devices (e.g., physiological sensors, etc.), and the like. Patient monitors can be portable devices that travel with the patient in order to provide continuous monitoring during care. When a patient arrives at a hospital room or other treatment location, the patient monitor is often plugged into or otherwise connected to a patient monitor mount. Patient monitor mounts provide a physical interface for the patient monitor and are generally fixed to the treatment location. Patient monitor mounts can also provide electrical connection to other devices or infrastructure, such as power to recharge patient monitor batteries, network connectivity to other medical devices or hospital computer systems, and the like.

During the course of providing healthcare to patients, practitioners typically connect at least one type of sensor to a patient to sense, derive or otherwise monitor at least one type of patient medical parameter. Such patient connected sensors are further connected to the monitor that includes all relevant electronic components that enable conversion, manipulation and processing of the data sensed by the at least one type of sensor in order to generate patient medical parameters. These patient medical parameters may be stored in one or more modules and are usable by healthcare practitioners (e.g., nurses, doctors, physician assistants, or any other person charged with providing a healthcare service to a patient) in monitoring a patient and determining a course of healthcare to be provided to the patient. Additionally, or alternatively, the one or more modules may contain data, such as patient treatment data, to be transferred to the monitor mount and/or the monitor.

The monitor may be selectively connected to a patient at any point during which a healthcare professional comes into contact with the patient and may remain connected with the patient as the patient moves through various locations within a particular healthcare enterprise (e.g., hospital) or between different healthcare enterprises (e.g., an ambulance and/or different medical facilities). The monitor and/or the module can allow data representing the at least one patient medical parameter to be communicated to other systems within the healthcare enterprise. This data may then be used by different systems in further patient care.

Patient monitors have different sizes and provide different functionalities. With current systems, each type of patient monitor typically requires a dedicated monitor mount, a dedicated controller, and a dedicated user interface. Accordingly, such monitors are not interoperable and the performance advantages of each type of monitor cannot be combined and leveraged.

In addition, there is a growing need in acute care environments to improve clinical workflow, reduce alarm fatigue, and customize medical devices to better suit hospital protocols and use models.

Due to the above problems associated with current systems, there is a need for a modular system providing a universal and scalable platform including a monitor mount capable of mixed use with monitors having different sizes which are interoperable with the same controller and the same user interface, and that can be universally docked to the monitor mount. Additionally, with the objective of providing a scalable platform, there is a need to facilitate mounting a smaller monitor to a larger monitor and/or a monitor mount from multiple directions to reduce the need for performing cumbersome maneuvers and to reduce cable clutter and entanglement that may impede patient care.

SUMMARY

Embodiments provide a patient monitor system having a mount, a smaller monitor (first monitor), and a larger monitor (second monitor) that is adapted to removably receive the smaller monitor, with the smaller monitor and/or the larger monitor configured to be removably attached to the mount alone or in combination, and to provide for data and power transfer between the monitors and the mount.

The monitor mount may detachably secure the second monitor, and the second monitor can detachably secure (or otherwise physically interface with) the first monitor. The first monitor may be first mounted or otherwise detachably secured to the second monitor to form an expanded monitor system, and the monitor system may be then detectably secured to the monitor mount. Alternatively, the second monitor may be first mounted or otherwise detachably secured to the monitor mount, and the first monitor may be subsequently inserted into or otherwise mounted within a mounting area defined by the second monitor, the monitor mount, or both the second monitor and the monitor mount. For example, the mounting area may be defined by a volume or cavity formed when the second monitor and the monitor mount are coupled together.

Therefore, the example system provides an interconnected, versatile, and comprehensive patient care solution with a high degree of configurability to accommodate different or dynamically changing environments. Accordingly, the example system thereby improves clinical workflow.

The monitor mount can detachably secure (or otherwise physically interface with) both of the first monitor and the second monitor, alone or in combination. The first monitor has a shape and size which differs from that of the second monitor. Nonetheless, both of the first monitor and the second monitor are able to be concurrently secured to the monitor mount.

BRIEF DESCRIPTION OF THE DRAWINGS

Embodiments are described herein making reference to the appended drawings.

DETAILED DESCRIPTION

Figure 1:
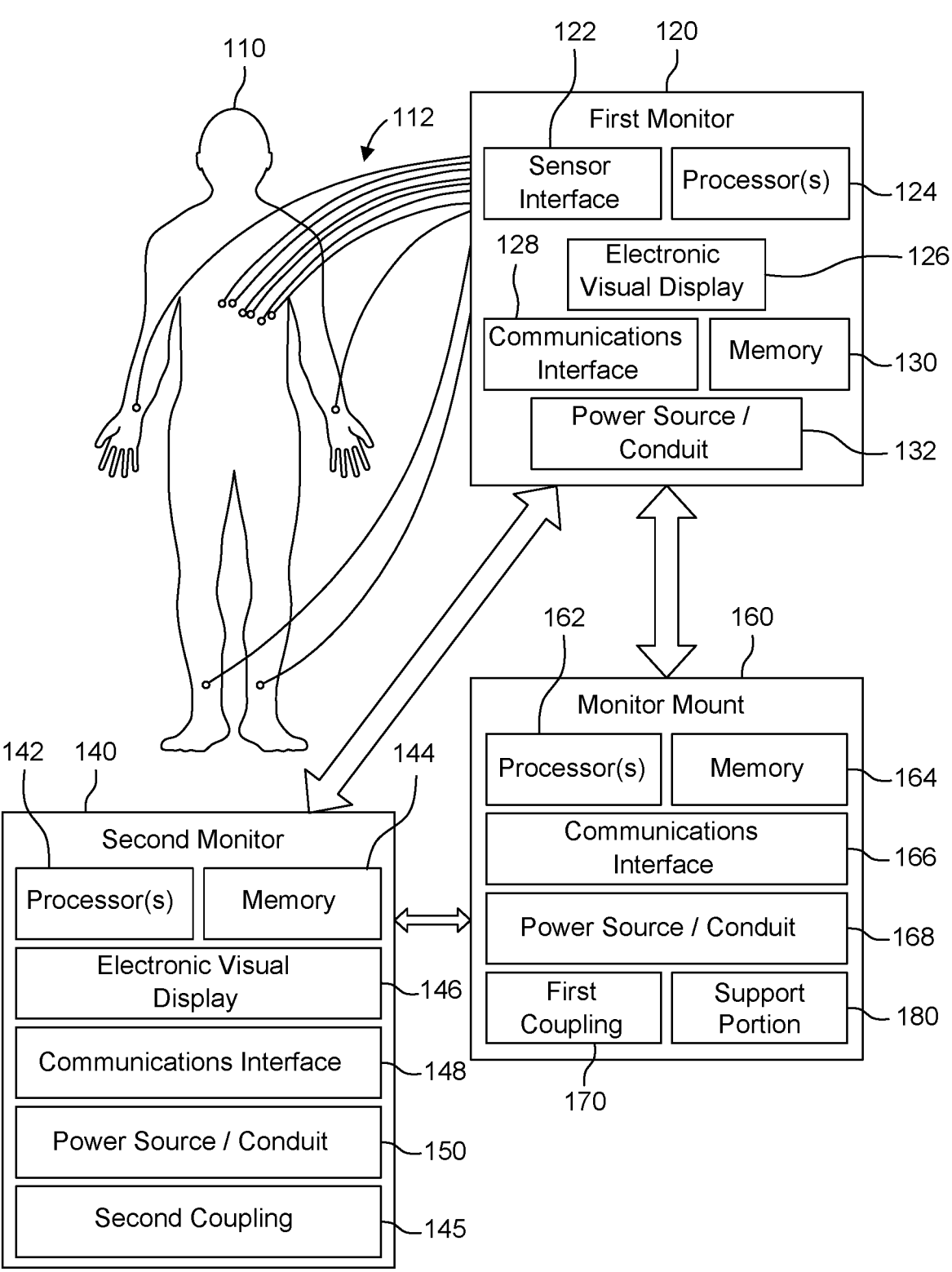
FIG. 1 is a logical diagram illustrating the example system including a first monitor, a second monitor, and a monitor mount.

The following detailed description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

For example, in the description of the figures that follow, the automatic power on apparatus, system, method, and circuit are implemented in patient monitors. However, it should be understood and appreciated by one of ordinary skill in the art that the automatic power on apparatus, system, method, and circuit of the present disclosure can be implemented in other medical or electronic devices. The implementation of the automatic power on apparatus, system, method, and circuit in the patient monitors is meant only to assist in the understanding of the present disclosure and in no way is meant to limit the implementation the automatic power on apparatus, system, method, and circuit described herein.

Additionally, the terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

Features from different embodiments may be combined to form further embodiments, unless specifically noted otherwise. Variations or modifications described with respect to one of the embodiments may also be applicable to other embodiments. In some instances, well-known structures and devices are shown in block diagram form rather than in detail in order to avoid obscuring the embodiments.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It is to be understood that the singular forms "a", "an", and "the", include plural referents unless the context clearly dictates otherwise. Thus, for example, reference to "a processor" or "a memory" includes reference to one or more of such processors or memories.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include"

and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

The subject matter described herein is directed to systems and apparatuses directed to monitors (e.g., display monitors having visual electronic displays) and monitor mounts providing physical support and, in some cases, power and access to a communications/computer network. Use of such systems and apparatuses can, for example, occur in a medical environment such as the scene of a medical event, an ambulance, a hospital or a doctor's office. When a patient undergoes initial patient monitoring in such an environment, a minimum set of sensors can be connected to a patient to collect various types of patient information (e.g., physiological information) as described in detail herein. As a patient is moved from one area of care within the medical environment to another area of care, the patient monitor can travel with the patient. In some situations, the patient monitor can be mounted to a monitor mount to provide for stationary observation of the patient information on a visual electronic display. During the course of patient monitoring, the number of sensors can also increase due to increased testing and/or monitoring of the patient. In such a scenario, a patient monitor initially monitoring the patient can be docked onto a monitor mount having a second, larger monitor in order to expand the number of sensors available for patient monitoring and/or increase the number of patient parameters on a single visual electronic display by docking the smaller patient monitor to or within a larger patient monitor. The initial patient monitor can either remain within the larger patient monitor or be removed from the larger patient monitor.

FIG. 1 is a logical diagram illustrating the example system including a first monitor 120, a second monitor 140, and a monitor mount 160. In an exemplary implementation, the monitor mount 160 may be detachably secured to a support structure (not shown) (e.g., a wall-mounted arm) via any attachment mechanism (not shown) such as a Video Electronics Standards Association (VESA) mounting interface adapted to an attachment mechanism in a hospital room in which a patient 110 is being monitored and/or treated via one or more modules, for example one or more physiological sensors and/or medical devices.

The monitor mount 160 may detachably secure the second monitor 140, and the second monitor 140 can detachably secure (or otherwise physically interface with) the first monitor 120. The first monitor 120 may be first mounted or otherwise detachably secured to the second monitor 140 to form a two monitor system, and the monitor system may be then detectably secured to the monitor mount 160. Alternatively, the second monitor 140 may be first mounted or otherwise detachably secured to the monitor mount 160, and the first monitor 120 may be subsequently inserted into or otherwise mounted within a mounting area defined by the second monitor 140, the monitor mount 160, or both the second monitor 140 and the monitor mount 160. For example, the mounting area may be defined by a volume or cavity formed when the second monitor 140 and the monitor mount 160 are coupled together.

Therefore, the example system provides an interconnected, versatile, and comprehensive patient care solution with a high degree of configurability. The example system acquires data at the bedside and on transport, without having to disconnect a patient as he or she is moved from care area to care area. The example system can be scaled depending on the patient's changing acuity level and medical devices can be customized to better suit hospital protocols and use models. Accordingly, the example system thereby improves clinical workflow.

The monitor mount 160 can detachably secure (or otherwise physically interface with) both of the first monitor 120 and the second monitor 140, alone or in combination. As will be described in further detail below, the first monitor 120 has a shape and size which differs from that of the second monitor 140. Nonetheless, both of the first monitor 120 and the second monitor 140 are able to be concurrently secured to the monitor mount 160.

The first monitor 120 can, for example, be a patient monitor that is used to monitor various physiological parameters for a patient 110. With such a variation, the first monitor 120 can include a sensor interface 122 that can be used to connect via wired and/or wireless interfaces to one or more physiological sensors and/or medical devices 112 (e.g., electrocardiogram (ECG) electrodes, oxygen saturation (SpO2) sensor, non-invasive blood pressure (NIBP), blood pressure cuffs, apnea detection sensors, end-tidal carbon dioxide (etCO2), respirators, temperature, and other similar physiological data.) associated with the patient 110. The first monitor 120 can include one or more processors 124 (e.g., programmable data processors, etc.) which can execute various instructions stored in memory 130 of the first monitor 120. Various data and graphical user interfaces can be conveyed to a user via an electronic visual display 126 included in the first monitor 120. This information can, for example, relate to the measured physiological parameters of the patient 110 and the like (e.g., ECG waveforms, blood pressure, heart related information, pulse oximetry, respiration information, temperature, etc.). Other types of information can also be conveyed by the electronic visual display 126. In some variations, the electronic visual display 126 includes a touch screen interface that allows a user of the first monitor 120 to input data and/or modify the operation of the first monitor 120.

The first monitor 120 can additionally include a communications interface 128 which allows the first monitor 120 to directly or indirectly (via, for example, the monitor mount 160) access one or more computing networks. The communications interface 128 can include, various network cards/interfaces to enable wired and wireless communications with such computing networks. The communications interface 128 can also enable direct (i.e., device-to-device, etc.) communications (i.e., messaging, signal exchange, etc.) such as from the monitor mount 160 to the first monitor 120.

The first monitor 120 can optionally also include a power source and/or conduit 132 that can be used to power the various components of the first monitor 120 (and optionally various components of the second monitor 140 and/or the monitor mount 160). The power source/conduit 132 can include a self-contained power source such as a battery pack and/or the power source/conduit 132 can include an interface to be powered through an electrical outlet (either directly or indirectly by way of the second monitor 140 and/or the monitor mount 160). In some variations, the first monitor 120 can only be powered and render information when secured or otherwise connected to one or more of the second monitor 140 and the monitor mount 160.

The second monitor 140 can include one or more processors 142 (e.g., programmable data processors, etc.) which can execute various instructions stored in memory 144 of the second monitor 140. Various data and graphical user interfaces can be conveyed to the user via an electronic visual display 146 included in the second monitor 140. This information can, for example, relate to the measured physiological parameters of the patient 110 and the like (e.g., blood pressure, heart related information, pulse oximetry, respiration information, thermoregulation, neonatal information, ventilator information, anesthesia information, incubation information, etc.) as received from the first monitor 120. Other types of information can also be conveyed by the electronic visual display 146. In some variations, the electronic visual display 146 includes a touch screen interface that allows a user of the second monitor 140 to input data and/or modify the operation of the second monitor 140.

The second monitor 140 can additionally include a communications interface 148 which allows the second monitor 140 to directly or indirectly (via, for example, the first monitor 120 and/or the monitor mount 160) access one or more computing networks. The communications interface 148 can include various network cards/interfaces to enable wired and wireless communications with such computing networks. The communications interface 148 can also enable direct (i.e., device-to-device, etc.) communications (i.e., messaging, signal exchange, etc.) such as from the monitor mount 160 to the second monitor 140 and the first monitor 120 to the second monitor 140.

The second monitor 140 can optionally also include a power source and/or conduit 150 that can be used to power the various components of the second monitor 140 (and optionally various components of the first monitor 120). The power source/conduit 150 can include a self-contained power source such as a battery pack and/or the power source/conduit 150 can include an interface to be powered through an electrical outlet (either directly or by way of the first monitor 120 and/or the monitor mount 160). In some variations, the second monitor 140 can only be powered and render information when secured or otherwise connected to one or more of the first monitor 120 and the monitor mount 160.

The second monitor 140 can include a second coupling 145 which is configured to detachably secure the first monitor 120. In some variations, the second coupling 145 may be positioned in a receptacle of the second monitor 140. The receptacle may be defined in a lateral direction of the second monitor 140 and have open side portions for receiving the first monitor 120. For example, the user can visually confirm the location of the second coupling 145 and transversely insert the first monitor 120 into the second monitor 140. In some variations, the receptacle may have an open top portion instead of open side portions such that the first monitor 120 can be dropped into the second monitor 140 from above; and removed (e.g., lifted out) from the second monitor 140 from above.

The monitor mount 160 can include one or more processors 162 (e.g., programmable data processors, etc.) which can execute various instructions stored in memory 164 of the monitor mount 160. The monitor mount 160 can additionally include a communications interface 166 which allows the monitor mount 160 to directly or indirectly access one or more computing networks. The communications interface 166 can include various network cards/interfaces to enable wired and wireless communications with such computing networks. The communications interface 166 can also enable direct (i.e., device-to-device, etc.) communications (i.e., messaging, signal exchange, etc.) such as with the first monitor 120 and/or the second monitor 140.

The monitor mount 160 can optionally also include a power source and/or conduit 168 that can be used to power the various components of the monitor mount 160 and/or the first monitor 120 and/or the second monitor 140 when secured to the monitor mount 160. The power source/conduit 168 can include a self-contained power source such as a battery pack and/or the power source/conduit 168 can include an interface to be powered through an electrical outlet.

Any of the processors 124, 142, 162 may acquire data from any of the monitor mount 160 and one or more of the monitors 120, 140 and store the acquired data in a memory and, upon connection of the monitor mount 160 and one or more of the monitors 120, 140, transfer the data stored in the memory to the monitor mount 160 or one or more of the monitors 120, 140. The data may include any of patient identification data including information identifying a patient; patient parameter data representing at least one type of patient parameter being monitored; and device configuration data including information associated with configuration settings for the monitor mount 160 and/or the one or more monitors 120, 140.

The monitor mount 160 can optionally also include any mounting interface, such as a VESA mounting interface for mounting the monitor mount at the bedside, from the ceiling, on a wall of the room, or even outside the room for isolation purposes.

The monitor mount 160 can optionally also include an interface configured to receive a connector of a cable or wired connection for connecting a module, a monitor, other external unit or the like.

The monitor mount 160 can optionally also include one or more recesses for facilitating removal of the first monitor 120 and/or the second monitor 140.

In some variations, the one or more processors 162 and the memory 164 are omitted such that the monitor mount 160 provides only physical support and optionally a power source.

The monitor mount 160 has a shape and size which allows the monitor mount 160 to detachably secure both of the first monitor 120 and the second monitor 140 such that the respective monitors 120 and 140 can be removed by the user when desired.

The monitor mount 160 can include a first coupling 170 to allow the first monitor 120 and/or second monitor 140 to be secured to the monitor mount 160. The monitor mount 160 is able to secure each of the first monitor 120 and the second monitor 140 individually or both of the first monitor 120 and the second monitor 140 concurrently. In other words, the first coupling 170 is configured to accept either the first monitor 120 or the second monitor 140 such that the monitor mount 160 is configured to mount the first monitor 120 alone, the second monitor 140 alone, or a combination of the first monitor 120 and the second monitor 140. The first coupling 170 can include any mechanical attachment means such as a ledge, a rail, a rib, an abutment, a cleat, and the like, or any combination thereof.

The first coupling 170 can additionally or alternatively include different securing mechanisms including magnetic and/or electromagnetic locking mechanisms which cause the first monitor 120 to selectively be secured to the monitor mount 160. In some cases, the first monitor 120 can slide into and out of the first coupling 170 from one or more lateral directions (i.e., from one or more sides of the monitor mount 160) while in other variations, the first monitor 120 can be mounted to and removed from the front face of the monitor mount 160. In some implementations, the first monitor 120 can both slide into and out of the first coupling 170 from one or more lateral directions and be mounted to and removed from the front face of the monitor mount 160.

The positioning of the first monitor 120 when secured to the monitor mount 160 can be such that the communications interface 128 on the first monitor 120 aligns with the communications interface 166 of the monitor mount 160 to allow, for example, a direct connection (e.g., electrical connection). In other variations, the communications interface 128 of the first monitor 120 exchanges data with the communications interface 166 of the monitor mount 160 wirelessly (via, for example, optical communication by way of respective optical windows on the first monitor 120 and the monitor mount 160). For example, both communication interfaces 128 and 166 may include bi-directional phototransceivers that are configured for bi-directional communication. The communications interface 128 of the first monitor 120 may be located on a back facing portion of the first monitor 120, whereas the communications interface 166 may be located on a front facing portion of the monitor mount 160 so that the back facing portion and the front facing portion face each other when the first monitor 120 is mounted to the monitor mount 160.

The positioning of the first monitor 120 when secured to the monitor mount 160 can also align the power source/conduit 132 of the first monitor 120 to be coupled to the power source/conduit 168 of the monitor mount 160 which causes the monitor mount 160 to power the first monitor 120.

The monitor mount 160 can include a support portion 180 to allow the second monitor 140 to be secured to the monitor mount 160. The support portion 180 may be positioned at a top of the monitor mount 160 or a bottom of the monitor mount 160. The support portion 180 can include any mechanical attachment means such as a ledge, a rail, a rib, an abutment, a cleat, and the like, or any combination thereof. The positioning of the second monitor 140 when secured to the monitor mount 160 can be such that the communications interface 148 on the second monitor 140 aligns with the communications interface 166 of the monitor mount 160 to allow, for example, a direct connection (e.g., electrical connection). In other variations, the communications interface 148 of the second monitor 140 exchanges data with the communications interface 166 of the monitor mount 160 wirelessly (via, for example, optical communication by way of respective optical windows on the second monitor 140 and the monitor mount 160). For example, both communication interfaces 128 and 166 may include bi-directional phototransceivers that are configured for bi-directional communication. These connections (electrical, optical, wireless, etc.) can be used to sense position (docking, undocking) as well as the type of monitor mount 160 out of a plurality of types of mounts. The communications interface 148 of the second monitor 140 may be located on a back portion of the second monitor 140. The communications interface 148 of the second monitor 140 may be located on a back facing portion of the second monitor 140, whereas the communications interface 166 may be located on a front facing portion of the monitor mount 160 so that the back facing portion and the front facing portion face each other when the second monitor 140 is mounted to the monitor mount 160.

The support portion 180 can enable front-to-back docking of the second monitor 140 to the monitor mount 160 by providing a shelf or similar feature extending outwardly. This feature of the support portion 180 can support and/or disperse the weight of the second monitor 140 during positioning of the second monitor 140. For example, a user attempting to position the second monitor 140 onto the monitor mount 160 can rest the second monitor 140 on the support portion 180 during the positioning while attaching the back portion of the second monitor 140 to the first coupling 170. The support portion 180 can support a bottom face of the second monitor 140.

Alternatively, or additionally, the support portion 180 can enable hanging or suspension of a handle of the second monitor 140 from the monitor mount 160 by providing any mechanical attachment means such as a ledge, a rail, a rib, an abutment, a cleat, and the like, or any combination thereof extending laterally from the top portion of mount 160. This feature of the support portion 180 can support and/or disperse the weight of the second monitor 140 during positioning of the second monitor 140. For example, a user attempting to position the second monitor 140 to the monitor mount 160 can hang or suspend the handle of the second monitor 140 from the support portion 180 during the positioning while attaching the back portion of the second monitor 140 to the first coupling 170.

The positioning of the second monitor 140 when secured to the monitor mount 160 can also align the power source/conduit 150 of the second monitor 140 to be coupled to the power source/conduit 168 of the monitor mount 160 which causes the monitor mount 160 to power the second monitor 140 or vice-versa. In some variations, the positioning of the second monitor 140 when secured to the monitor mount 160 and/or when the first monitor 120 is also secured to the monitor mount 160 can also align the power source/conduit 150 of the second monitor 140 to be coupled to the power source/conduit 132 of the first monitor 120 (which in turn is connected to the power source/conduit 168 of the monitor mount 160) which causes the first monitor 120 to power the second monitor 140.

The modular mounting of the three devices 120, 140, and 160 will now be described in greater detail. The modular mounting may allow the first monitor 120 to dock into the monitor mount 160 from the mount's front surface, allow the first monitor 120 to dock into the monitor mount 160 by sliding the first monitor 120 in from the left and/or the right lateral side of the monitor mount 160, allow the combination of the first monitor 120 and the second monitor 140 to dock to the monitor mount 160, allow the first monitor 120 to slide out of the combination of the monitor mount 160 and the second monitor 140 while the monitor mount 160 and the second monitor 140 remain mechanically coupled to one another, allow the second monitor 140 to be mounted to the monitor mount 160 in the absence of the first monitor mount 120, and any combination thereof.

FIGS. 2A-2F show various mounting arrangements of the modular system 200 comprising of the first monitor 120, the second monitor 140, and the monitor mount 160 according to one or more embodiments.

Figure 2A:
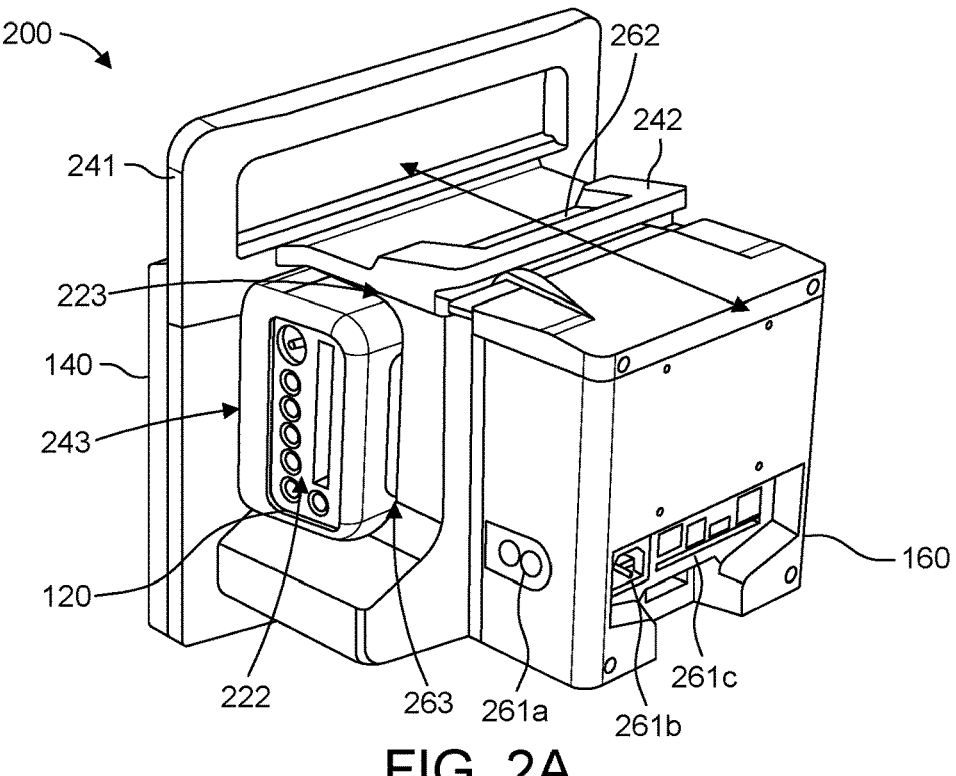
FIGS. 2A-2F show various mounting arrangements of the modular system comprising of the first monitor, the second monitor, and the monitor mount according to one or more embodiments.
Figure 2B:
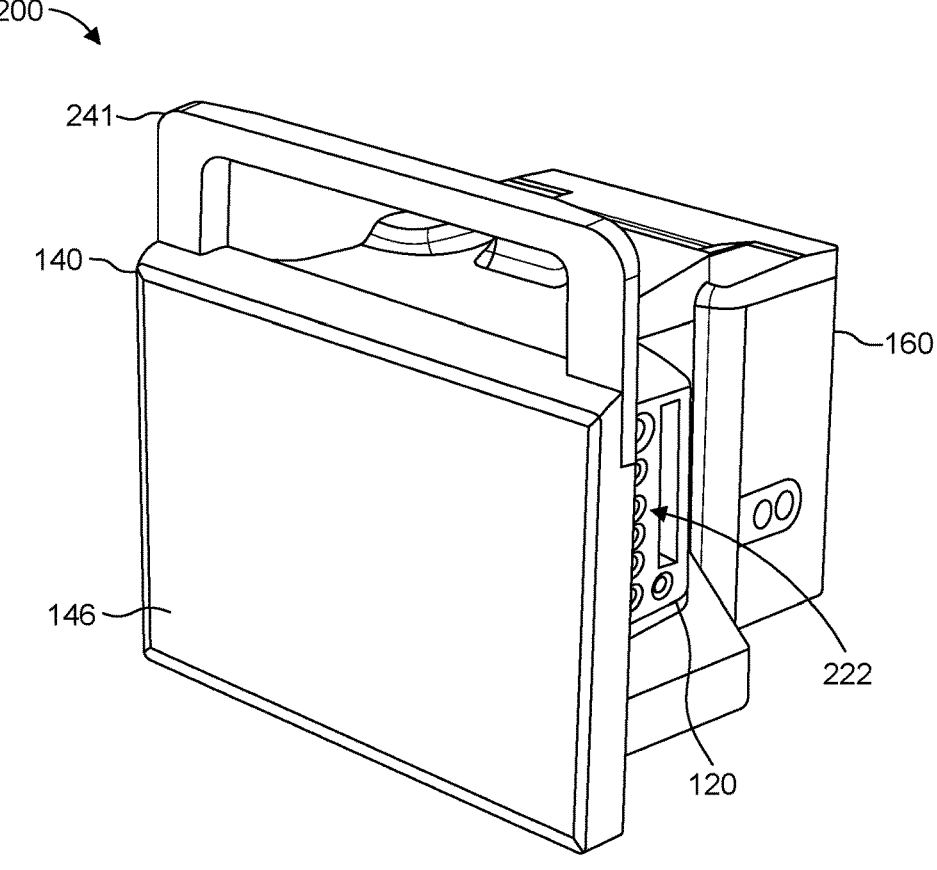

FIG. 2A is a rear perspective view of all three devices 120, 140, and 160 coupled together. FIG. 2B is a front perspective view of all three devices 120, 140, and 160 coupled together. The second monitor 140 includes the electronic visual display 146 at its front side and a handle 241 at its top side to facilitate user handling of the unit. It will be appreciated that the placement of the handle may vary and two or more handles may also be provided. The second monitor 140 further includes a coupling mechanism 242 such as a cleat that extends from the handle 241 and is configured to mechanically engage with and couple to the monitor mount 160. The monitor mount 160 includes a corresponding coupling mechanism 262 such as a latch that mechanically engages with coupling mechanism 242. The two coupling mechanisms 242 and 262 are mechanically interlocked with each other by maneuvering at least one of the two devices 140 and 160 in the direction of the arrow that the two coupling mechanisms 242 and 262 are brought into contact.

The second monitor 140 has a rear mounting area 243 at which the first monitor 120 can be received and mounted. Similarly, the monitor mount 160 has a front mounting area 263 at which the first monitor 120 can be received and mounted. When the second monitor 140 is mounted to the monitor mount 160, the rear mounting area 243 and the front mounting area 263 define a volume or a cavity 223 in which the first monitor 120 can be mounted, inserted, or otherwise arranged. The cavity 223 may be referred to as a tunnel.

Various connector ports are also shown. For example, the first monitor 120 includes various connector ports 222 as part of its sensor interface 122 that are arranged on one lateral side of the unit. The monitor mount 160 includes network ports 261a for connecting to a computing network, a power port 261b for connecting to a power source, and input/output (I/O) ports 261c for connecting to external I/O devices and peripherals.

Figure 2C:
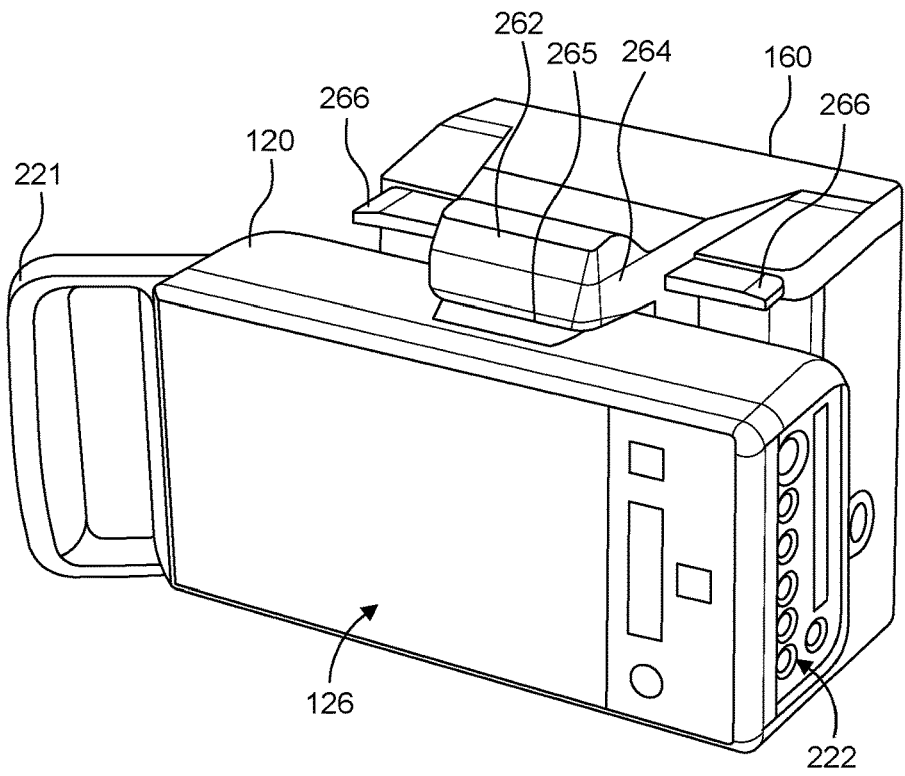
Figure 2D:
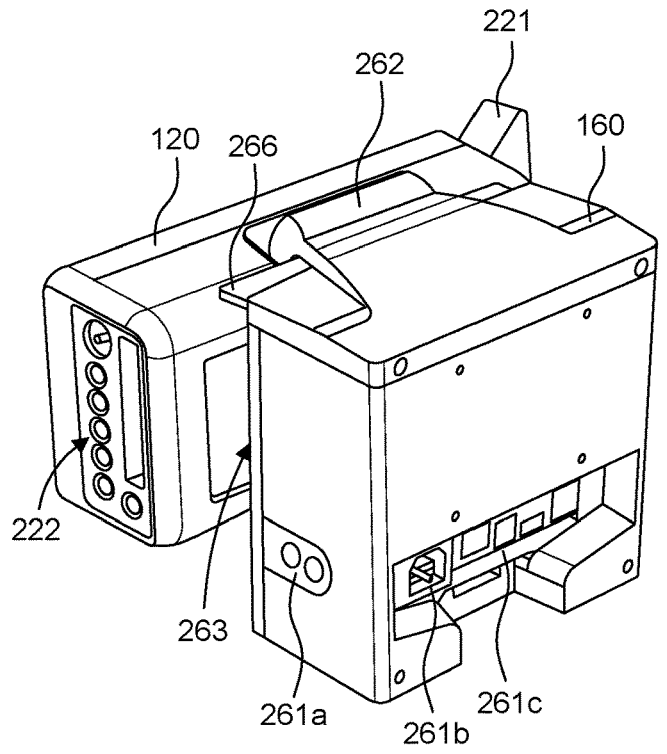

FIG. 2C is a front perspective view of the first monitor 120 and the monitor mount 160 coupled together without the second monitor 140. FIG. 2D is a rear perspective view of the first monitor 120 and the monitor mount 160 coupled together without the second monitor 140.

As can be seen here, the first monitor 120 includes the electronic visual display 126 at its front side and a handle 221 at the lateral side arranged opposite to the side at which the connector ports 222 are located. The handle 221 facilitates handling of the first monitor 120 and the mounting of the first monitor 120 into the various configurations described herein. However, the handle 221 is optional and may be omitted to reduce the footprint of the first monitor 120.

The coupling mechanism 262 of the monitor mount 160 is also shown. The coupling mechanism 262 is arranged on a top side of a mechanical arm 264 that extends outward from the main body of the monitor mount 160. The arm 264 defines, at least in part, the mounting area 263 into which the first monitor 120 is received. The underside of the arm 264 includes a coupling mechanism 265, such as a latch, that mechanically engages with and couples to a corresponding coupling mechanism, coupling structure, or coupling area (not shown) of the first monitor 120. The monitor mount 160 further includes latching release paddles 226 configured to disengage the coupling mechanism 265 from the first monitor 120 for undocking the first monitor 120 from the monitor mount 160.

Figure 2E:
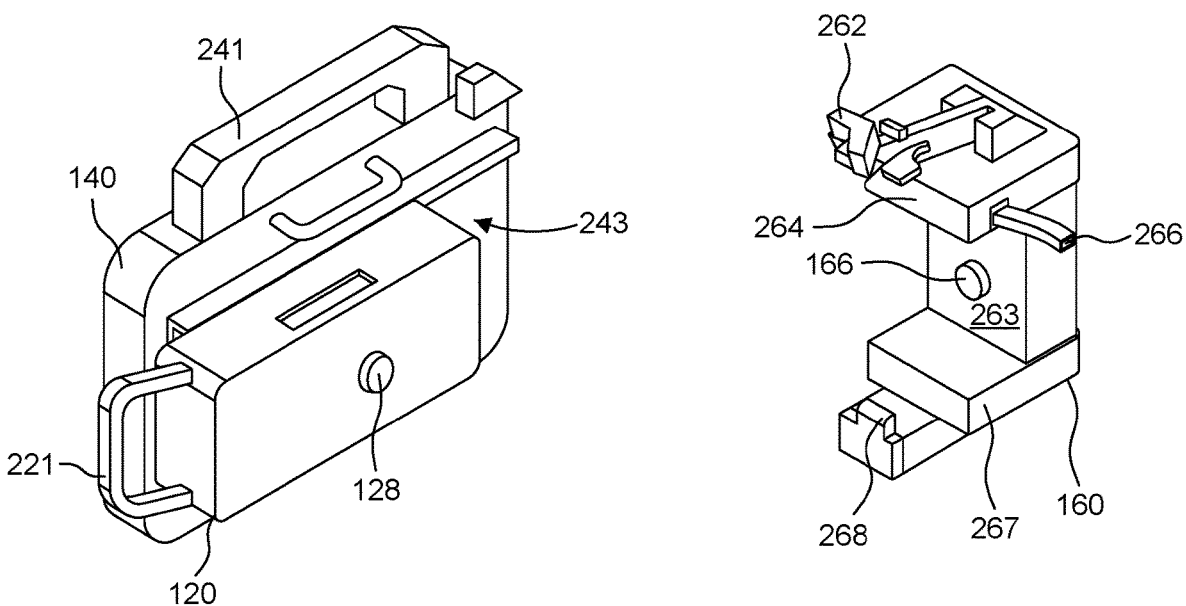

FIG. 2E is a rear perspective view of monitors 120 and 140 coupled together and detached from the monitor mount 160. As can be seen here, the first monitor 120 includes its communications interface 128 at its rear side and the monitor mount 160 includes its communication interface 166 at its front side and arranged to be in alignment with communications interface 128 when the first monitor 120 is mounted to the monitor mount 160.

The monitor mount 160 further includes a mechanical arm 267 that extends from the body of the monitor mount 160. Together, arms 264 and 267 define the mounting area 263. The mounting area 263 is a recessed area into which the first monitor 120 can be inserted for mounting to the monitor mount 160. The mechanical arm 267 further includes another coupling mechanism 268 that is configured to engage with and couple to a bottom portion of the first monitor 120.

Figure 2F:
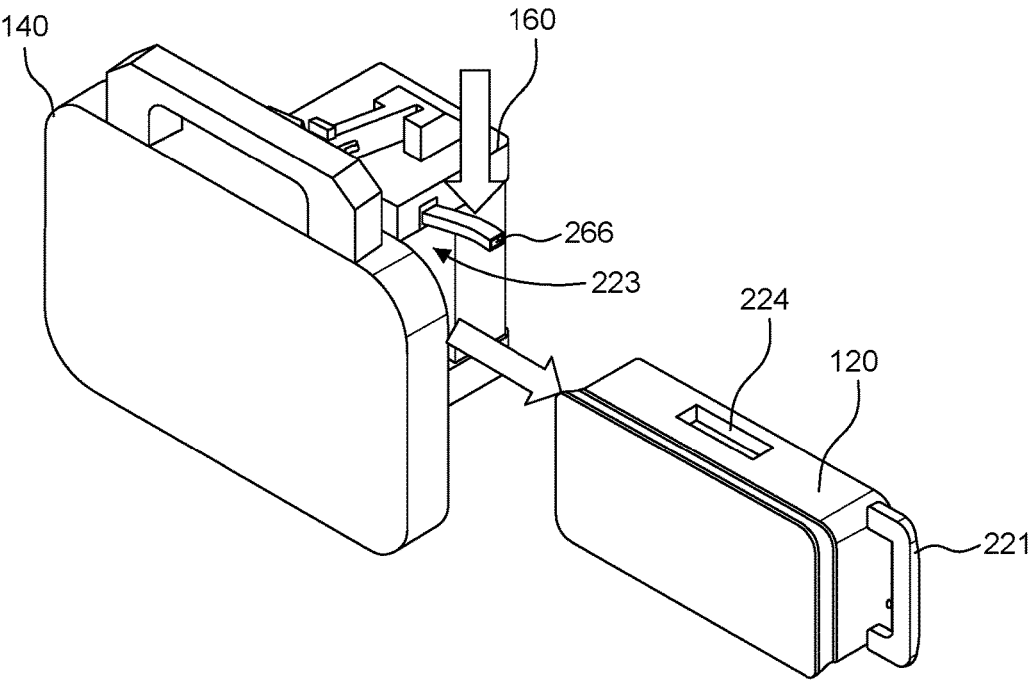

FIG. 2F is a front perspective view of all three devices 120, 140, and 160 during an undocking maneuver or separation maneuver of the first monitor 120 while the second monitor 140 remains mounted to the monitor mount 160. Here, the first monitor 120 is released from the coupling mechanism 265 by depressing the latching release paddle 266. Once the first monitor 120 is released from the coupling mechanism 265, it can by pulled out of the cavity 223 in a lateral direction by using, for example, the handle 221 of the first monitor 120. One-handed docking and undocking of the first monitor 120 may also be performed without using the handle, which may or may not be present.

Here, a coupling area 224 of the first monitor 120 can be seen. In this example, the coupling area 224 is a recess configured to receive or otherwise engage with the coupling mechanism 265 of the monitor mount 160 to be interlocked therewith in order to detachably secure the first monitor 120 to the monitor mount 160. The first monitor 120 may also include a second coupling area (not illustrated) at its underside to engage with coupling mechanism 268 for detachably securing the first monitor 120 to the monitor mount 160.

It will also be appreciated that the first monitor 120 may be inserted and removed from the other lateral (left) side of the modular assembly. For insertion on the other lateral side, the first monitor 120 can be rotated 180 degrees so that the handle 221 is outward facing from the cavity 223. The side having ports 222 is inserted into cavity 223 first regardless of whether the first monitor 120 is inserted from the left side or the right side. Also, the display 126 faces the rear side of the second monitor 140 and the communications interface 128 faces and is aligned with the communications interface 166 regardless of whether the first monitor 120 is inserted from the left side or the right side. The handle 221 is used for both insertion of the first monitor 120 into cavity 223 and for removal therefrom, which can be done by one hand. The placement of the coupling areas of the first monitor 120 help ensure that the communications interface 128 is aligned with the communications interface 166 when the coupling mechanisms 265 and 268 are engaged therewith.

Figure 3A:
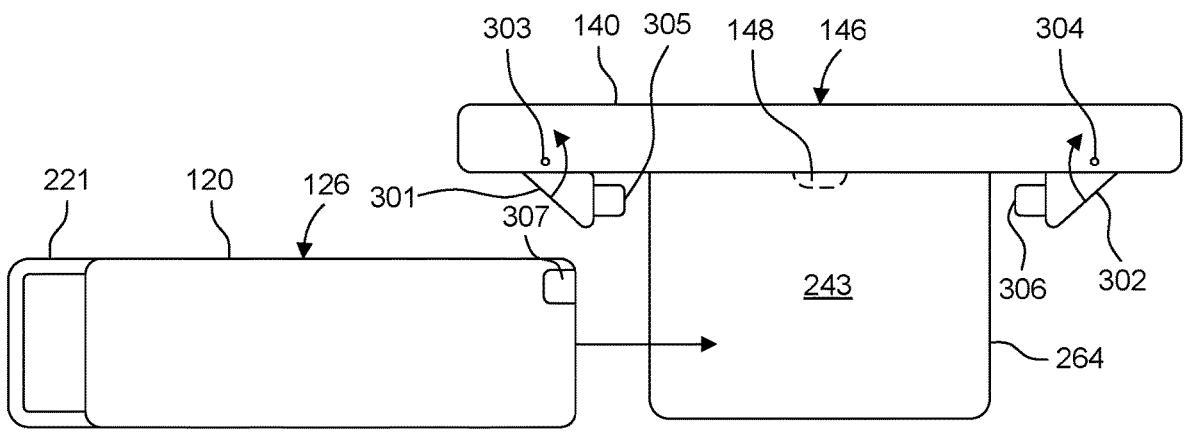
FIGS. 3A-3C are top views of part of the modular system that includes the first monitor and the second monitor and further illustrates a mounting or docking maneuver to mechanically and electrically couple the first monitor and the second monitor together.
Figure 3B:
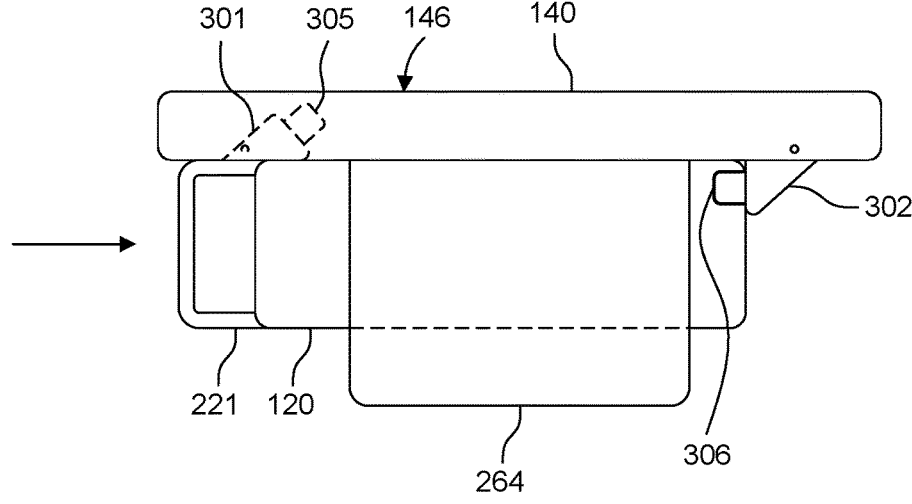
Figure 3C:
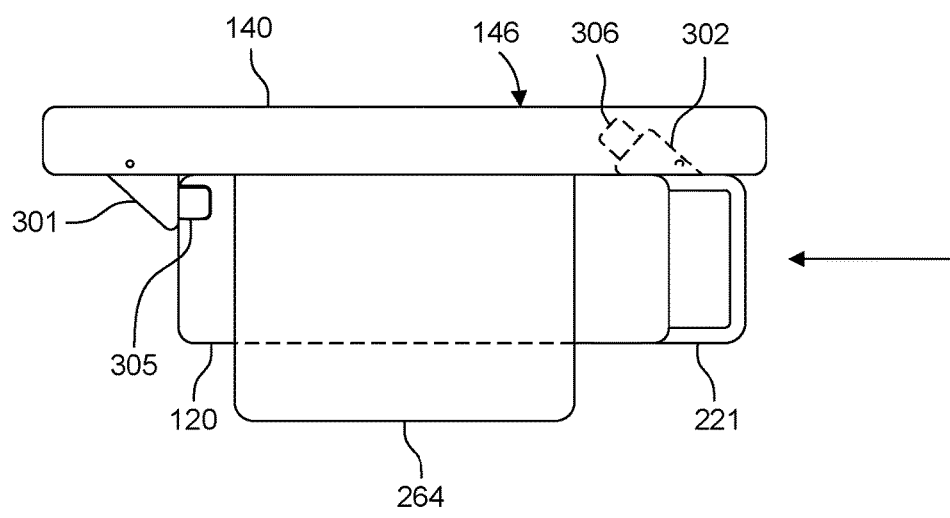

FIGS. 3A-3C are top views of part of the modular system 200 that includes the first monitor 120 and the second monitor 140 and further illustrates a mounting or docking maneuver to mechanically and electrically couple the first monitor 120 and the second monitor 140 together.

The second monitor 140 includes the electronic visual display 146 at its front side and the communications interface 148 at its rear side. The communications interface 148 is arranged to be aligned and in communication with the communications interface 166 of the monitor mount 160 when the first monitor 120 is not present (i.e., when the first monitor mount 120 is not inserted into cavity 223).

The second monitor 140 further includes two pivoting connectors 301 and 302 that each pivot on a respective pivot point 303 and 304. Each of the pivoting connectors 301 and 302 are configured to pivot into a respective recess that extends into the housing of the second monitor 140, as illustrated in FIG. 3B. Each of the pivoting connectors 301 and 302 are configured to pivot into its respective recess such that it is folded out of the way of the first monitor 120 and hidden from view. Each of the pivoting connectors 301 and 302 may be spring loaded such that the spring outward when not pushed into their respective recess by, for example, the first monitor 120.

Each of the pivoting connectors 301 and 302 includes a respective electrical interface 305 and 306 that is configured to electrically couple to a corresponding electrical interface 307 (e.g., a connector port) of the first monitor 120. A second electrical interface of the first monitor 120 is not shown but would be present for connecting with electrical interface 305 when the first monitor 120 is rotated 180 degrees for insertion from the right side.

The electrical connections made by electrical interfaces of the first monitor 120 and the second monitor 140 may be used to transfer information from the first monitor 120 to the second monitor 140 for display on the electronic visual display 146. As stated above, this information can include any type of patient information, including physiological information generated by the first monitor 120 that is derived from one or more physiological sensors connected to a patient.

The electrical connections made by electrical interfaces of the first monitor 120 and the second monitor 140 may also be used to transfer power from the first monitor 120 to the second monitor 140, or vice versa, in order to supply power to the components of the second monitor 140 or to the components of the first monitor 120. When the first monitor 120 is mounted to the monitor mount 160, the electrical connections may be used to transfer part of the power that the first monitor 120 receives from the monitor mount 160 to the second monitor 140. Recharging of the power sources 132 and 150 may also be enabled through these electrical connections.

The rear mounting area 243 of the second monitor 140 is located underneath the mechanical arm 264 and is represented in a dashed-line form to indicate that is hidden from the top view. The first monitor 120 is inserted into the rear mounting area 243 it is slid underneath the mechanical arm 264, as previously illustrated.

As the first monitor 120 is being inserted into the rear mounting area 243 of the second monitor 140 from the left lateral side and moved laterally through the rear mounting area 243 in the right lateral direction, as shown in FIG. 3B, it makes mechanical contact with the pivoting connector 301 and pushes it out of the way so that it completely resides within its recess. As a result, the pivoting connector 301 moves into its recess without obstruction to the first monitor 120. The first monitor 120 is inserted into the rear mounting area 243 until its electrical interface 307 engages with the electrical interface 306 of the second monitor 140.

Similarly, as shown in FIG. 3C, as the first monitor 120 is being inserted into the rear mounting area 243 of the second monitor 140 from the right lateral side and moved laterally through the rear mounting area 243 in the left lateral direction, it makes mechanical contact with the pivoting connector 302 and pushes it out of the way so that it completely resides within its recess. As a result, the pivoting connector 302 moves into its recess without obstruction to the first monitor 120. The first monitor 120 is inserted into the rear mounting area 243 until its other electrical interface (not illustrate) engages with the electrical interface 305 of the second monitor 140.

As a result of this dual-entry configuration, the first monitor 120 can be inserted from either lateral side of the second monitor 140 to facilitate the mounting of the first monitor 120 to the second monitor 140. The dual-entry configuration also provides flexibility in a dynamic patient environment where the location of patent and medical instruments, sensors, and devices can vary from location to location. This helps to not only reduce cable clutter and entablement, but generally facilitates the coupling to the two monitors in a way that is best suited for the current patient environment.

It will be further appreciated that signaling between monitors 120 and 140 may also be achieved using radio frequency (RF) links that would allow data connections to be wireless. However, physical connectors 301 and 302 could still be used for power distribution. In addition, the link between monitors 120 and 140 could be entirely wireless. For example, the interface may include a magnetic coupling for power, RF for communications, and an opto-couplers for status.

Figure 3D:
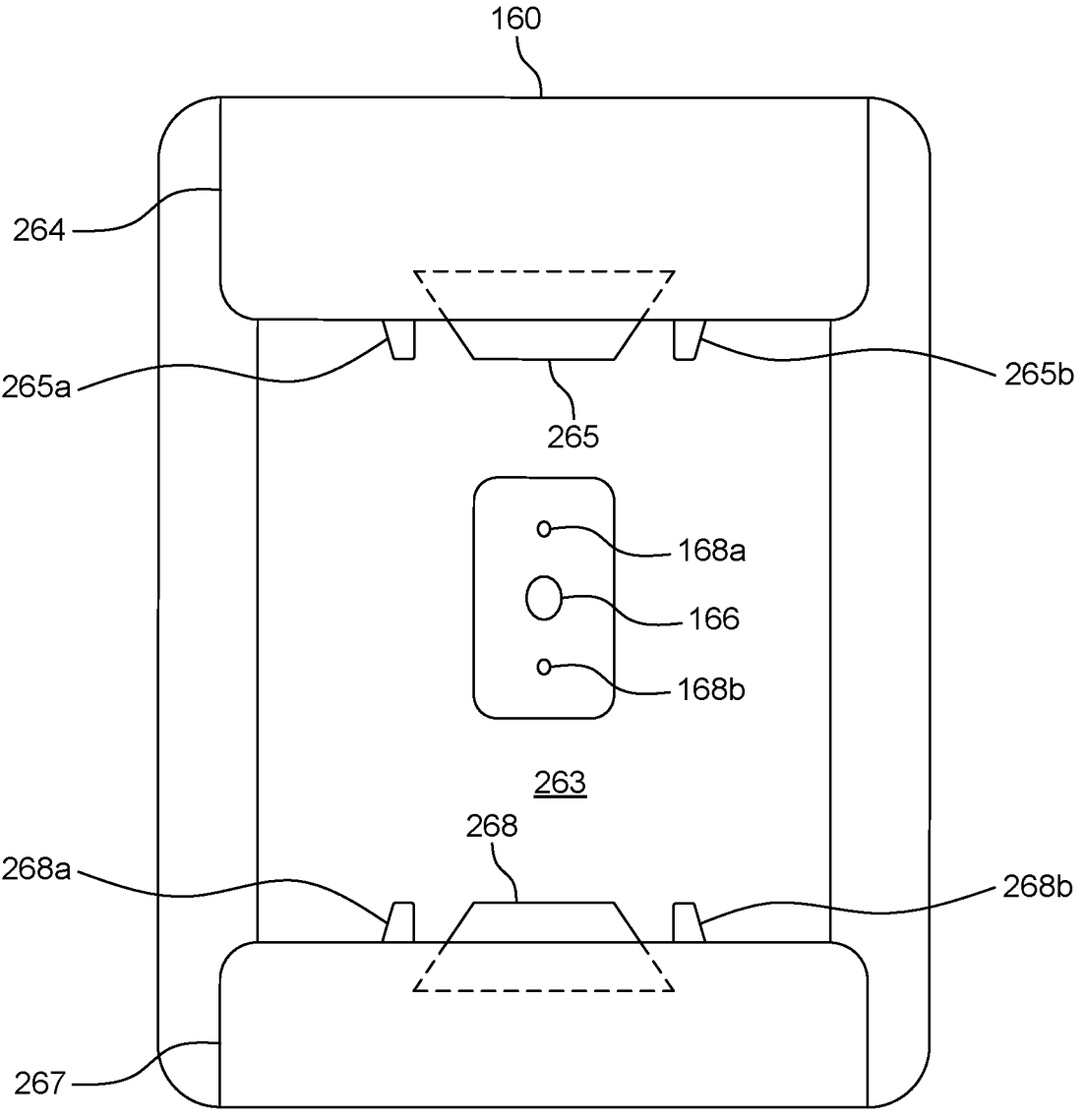
FIG. 3D is a front view of part of the modular system that includes the monitor mount.

FIG. 3D is a front view of part of the modular system 200 that includes the monitor mount 160. Mechanical arms 264 and 267 define the front mounting area 263 into which the first monitor 120 can be inserted, either in alone or while mounted to the second monitor 140. For example, the assemblies shown in FIGS. 3B and 3C can be mounted to the monitor mount 160, with the first monitor 120 being inserted into the front mounting area 263, between the arms 264 and 267.

Coupling mechanisms 265 and 268 are also shown. Here, the coupling mechanisms 265 and 268 are retractable latches that can be retracted via one of the latching release paddles 266 for releasing the first monitor 120 from the latches 265 and 268. Additional latches 265a, 265b, 268a, and 268b can also be included to provide for extra stability for mounting the first monitor 120 to the monitor mount 160.

The communications interface 166 of the monitor mount 160 is also shown, located at the front face of the monitor mount 160 with the front mounting area 264. The communications interface 166 is an optical transceiver that is configured to aligned with a corresponding optical transceiver of the communications interfaces 128 and 148 for exchanging communications and data. The monitor mount 160 further includes conduit 168 that includes a power contact 168a and a ground contact 168b that are used to supply power to the first monitor 120 when mounted to the monitor mount 160. When the first monitor 120 is mounted to the monitor mount 160, its power and ground contacts of conduit 132 are in electrical interface with the power contact 168a and the ground contact 168b, respectively.

Figure 4:
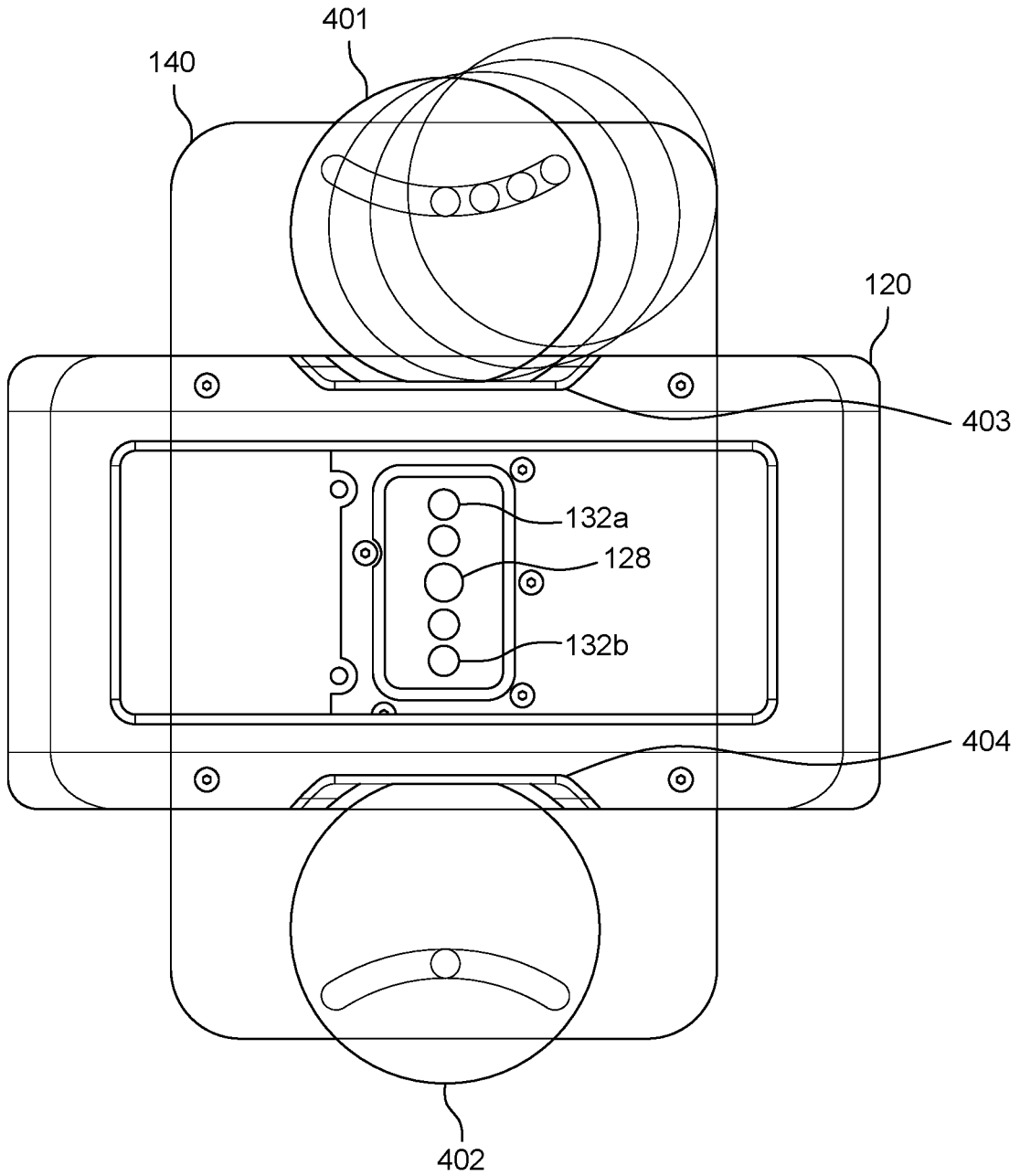
FIG. 4 is a front view of part of the modular system that includes the first monitor and the second monitor and further illustrates a mounting or docking to mechanically and electrically couple the first monitor and the second monitor together.
Figure 5A:
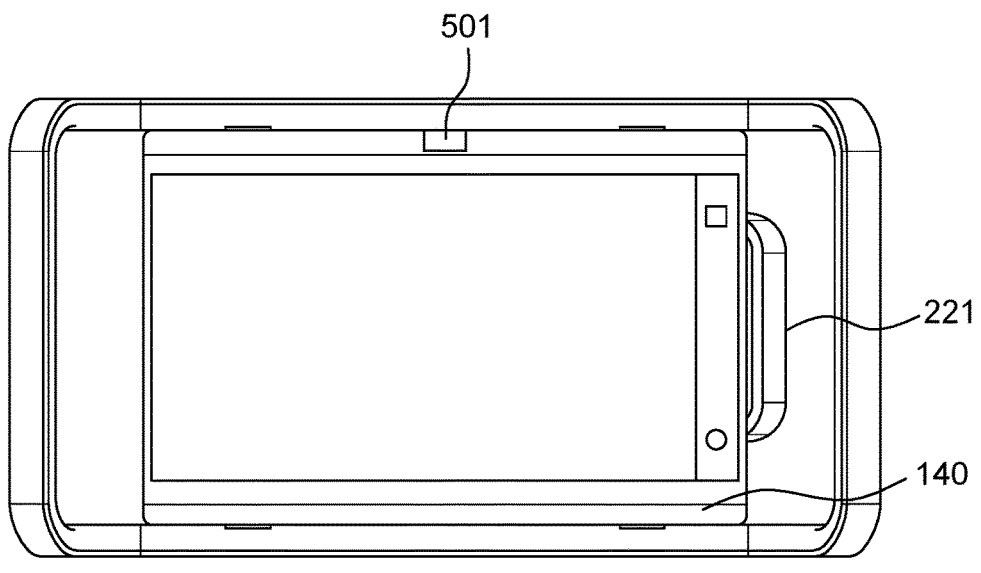
FIGS. 5A-5F show various show various mounting arrangements of the modular system comprising of the first monitor, the second monitor, and the monitor mount according to one or more embodiments.
Figure 5B:
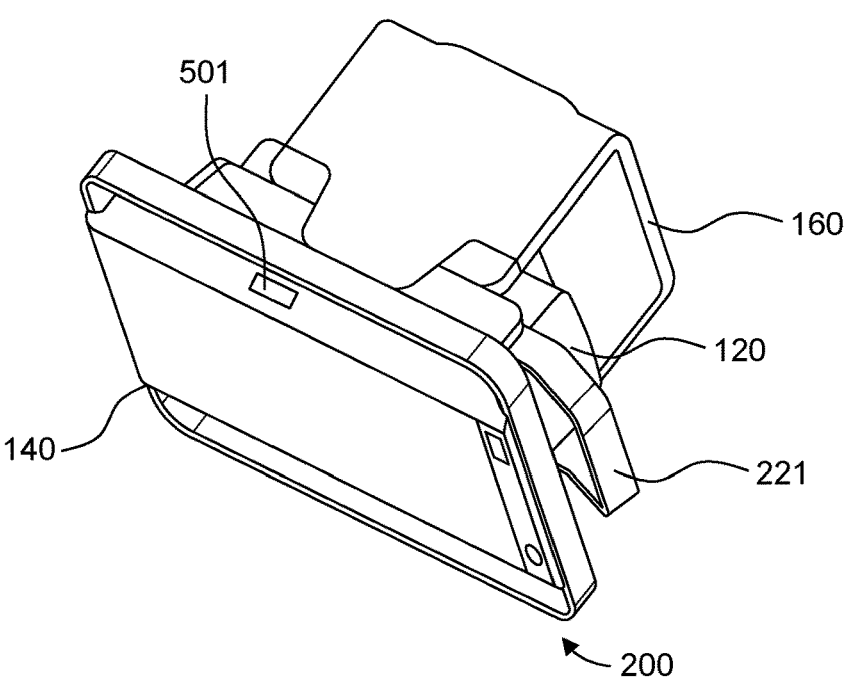
Figure 5C:
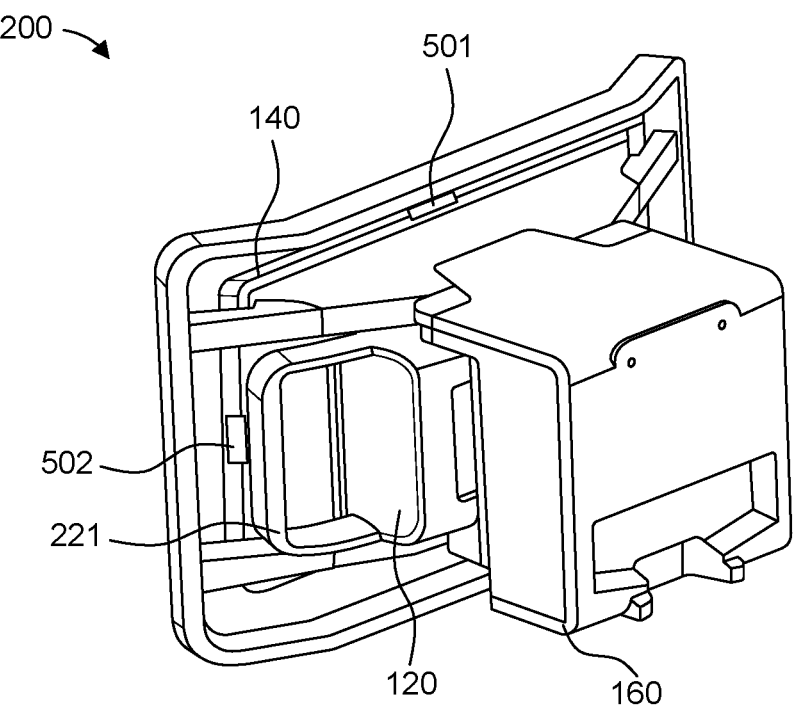
Figure 5D:
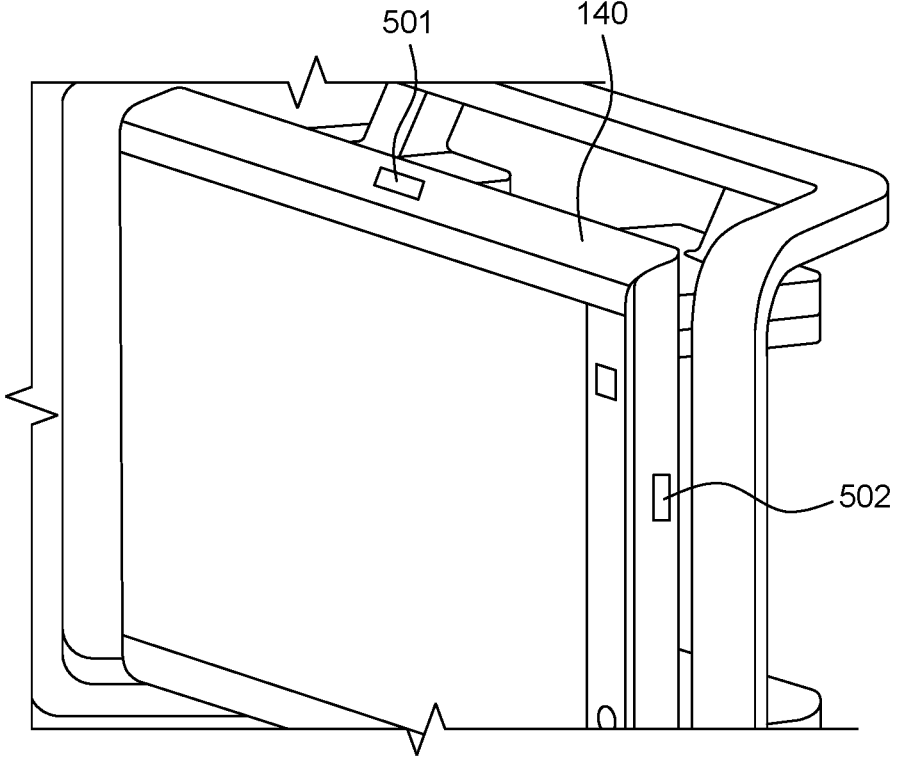
Figure 5E:
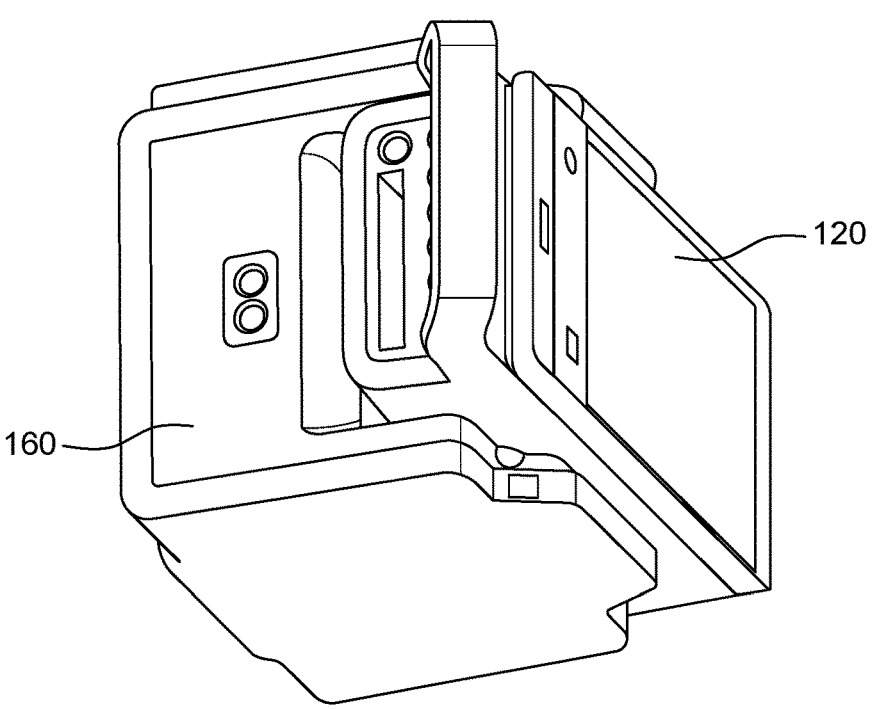
Figure 5F:
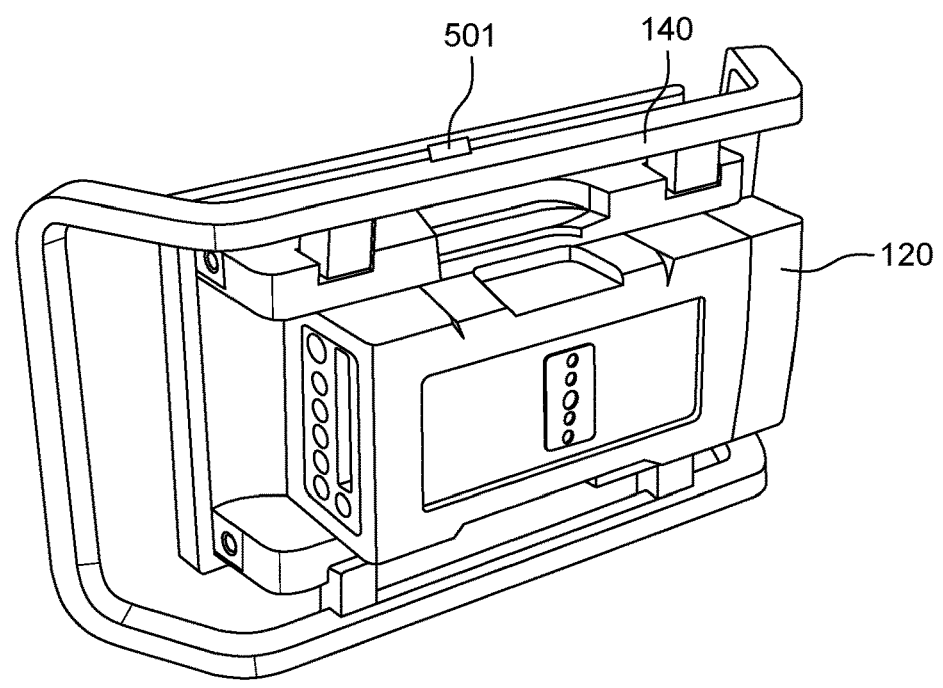

FIG. 4 is a front view of part of the modular system 200 that includes the first monitor 120 and the second monitor 140 and further illustrates a mounting or docking to mechanically and electrically couple the first monitor 120 and the second monitor 140 together. FIG. 4 illustrates another type of coupling mechanism that enables the first monitor 120 to be mounted to the second monitor 140, within the rear mounting area 243 thereof. The communications interface 128 of the first monitor 120 is also shown, located at its rear face.

The communications interface 128 is an optical transceiver that is configured to aligned with a corresponding optical transceiver of the communications interface 166 for exchanging communications and data. The first monitor 120 further includes conduit 132 that includes a power contact 132a and a ground contact 132b that are used to receive power from the monitor mount 160 when mounted thereto. When the first monitor 120 is mounted to the monitor mount 160, its power and ground contacts of conduit 132 are in electrical interface with the power contact 168a and the ground contact 168b, respectively.

The coupling mechanism of the second monitor 140 enables the first monitor 120 to be slide into and out of the rear mounting area 243 and includes a first rotatable clamp 401 and a second rotatable clamp 402. The rotatable clamps 401 and 402 are circular structures that are configured to rotate or pivot away from a center, rest position to allow the first monitor 120 to be inserted into or extracted from the rear mounting area 243. The rotatable clamps 401 and 402 can rotate away from the center position in either the clockwise or counter-clockwise position to allow for the first monitor to move laterally in either direction for dual-entry and exit.

When the first monitor 120 is arranged in its final mounted position, the rotatable clamps 401 and 402 can be locked into place, thereby clamping the first monitor 120 into position.

The first monitor 120 incudes recesses 403 and 404 (e.g., grooves) that are configured to receive a portion of one of the rotatable clamps 401 and 402. The recesses 403 and 404 function in a similar way to coupling area 224 in that they are used to engage with the coupling mechanism of the second monitor 140 to lock the first mount 120 within the rear mounting area 243. For removal, the rotatable clamps 401 and 402 can be unlocked (e.g., by one of the latching release paddles 266) so that the first monitor 120 can be slid out of the rear mounting area 243. When unlocked, the rotatable clamps 401 and 402 rotate away from the center, locking position as the first monitor 120 is being removed. The rotatable clamps 401 and 402 automatically return to the center position when no counter force is being applied thereto.

FIGS. 5A-5F show various show various mounting arrangements of the modular system 200 comprising of the first monitor 120, the second monitor 140, and the monitor mount 160 according to one or more embodiments. Here, the second monitor includes two solenoid buttons 501 and 502 that are used for undocking. In particular, solenoid button 501 is used to undock the second monitor 140 from the monitor mount 160 while leaving the first monitor 120 docked to the second monitor 140 if docked thereto. Solenoid button 502 is used to undock the first monitor 120 from the second monitor 140. The latching mechanisms controlled by the two solenoid buttons 501 and 502 are hidden in the handles of the second monitor 140. Thus, they are part of the second monitor 140 and not part of the mount 160. This allows the mount 160 to achieve a smaller size relative to the large monitor 140.

FIGS. 6A-6E are various perspective views of part of the modular system 200 that includes the first monitor 120 and the second monitor 140 and further illustrates a mounting or docking maneuver to mechanically and electrically couple the first monitor 120 and the second monitor 140 together.

The system includes a removably interchangeable connector block 601 that includes a first electrical interface 602 that is electrically connected to the first monitor 120 and a second electrical interface 603 that is electrically connected to the second monitor 140. The two electrical interfaces 602 and 603 are arranged at surfaces orthogonal to each other and are electrically connected to each other within the connector block 601 in order to transfer data signals and power signals therebetween. Electrical interface 602 is configured to be, for example, electrically coupled to an electrical interface of the first monitor 120, such as electrical interface 307. Electrical interface 603 is configured to be coupled to electrical interfaces 305 or 306 of the second monitor 140. Thus, the connector block 601 is configured as an electrical conduit between the first monitor 120 and the second monitor 140. It can also assist in the docking of the first monitor 120 to the second monitor 140.

Figure 6A:
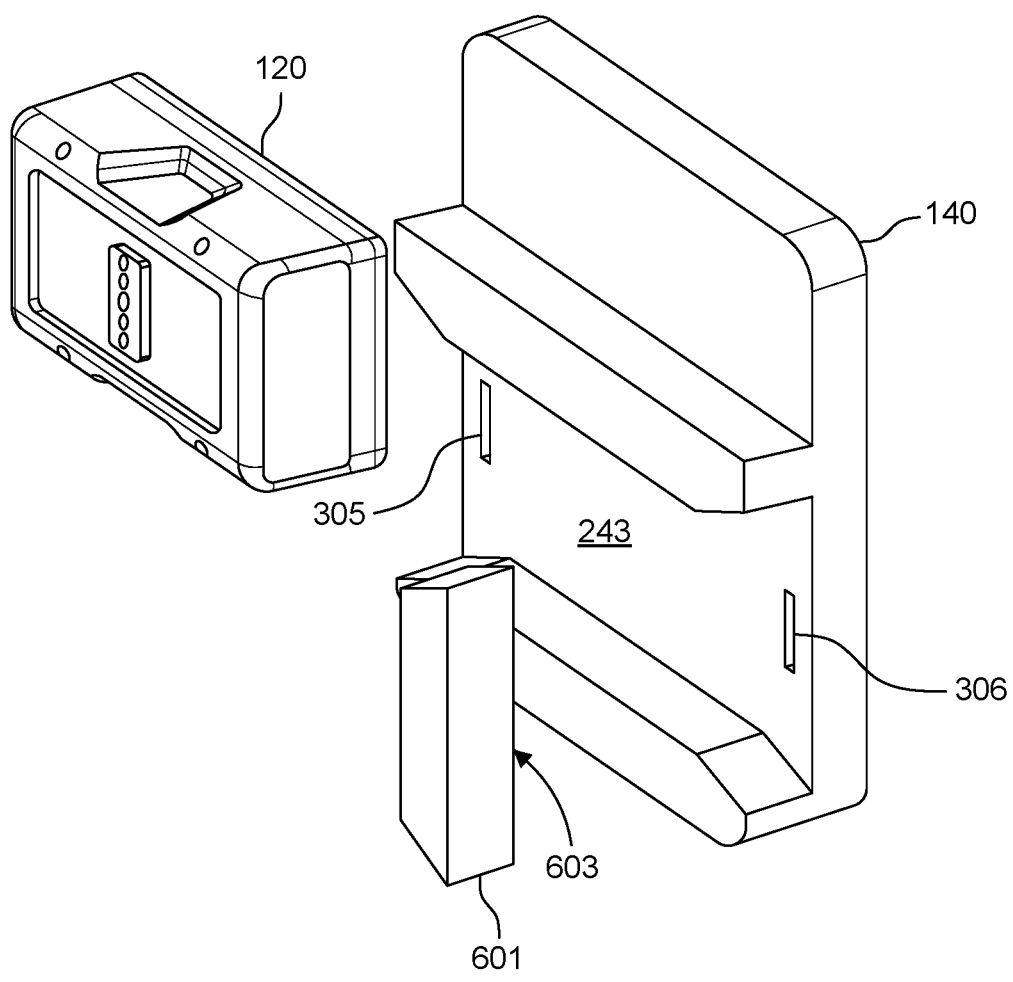
FIGS. 6A-6E are various perspective views of part of the modular system that includes the first monitor and the second monitor and further illustrates a mounting or docking maneuver to mechanically and electrically couple the first monitor and the second monitor together.
Figure 6B:
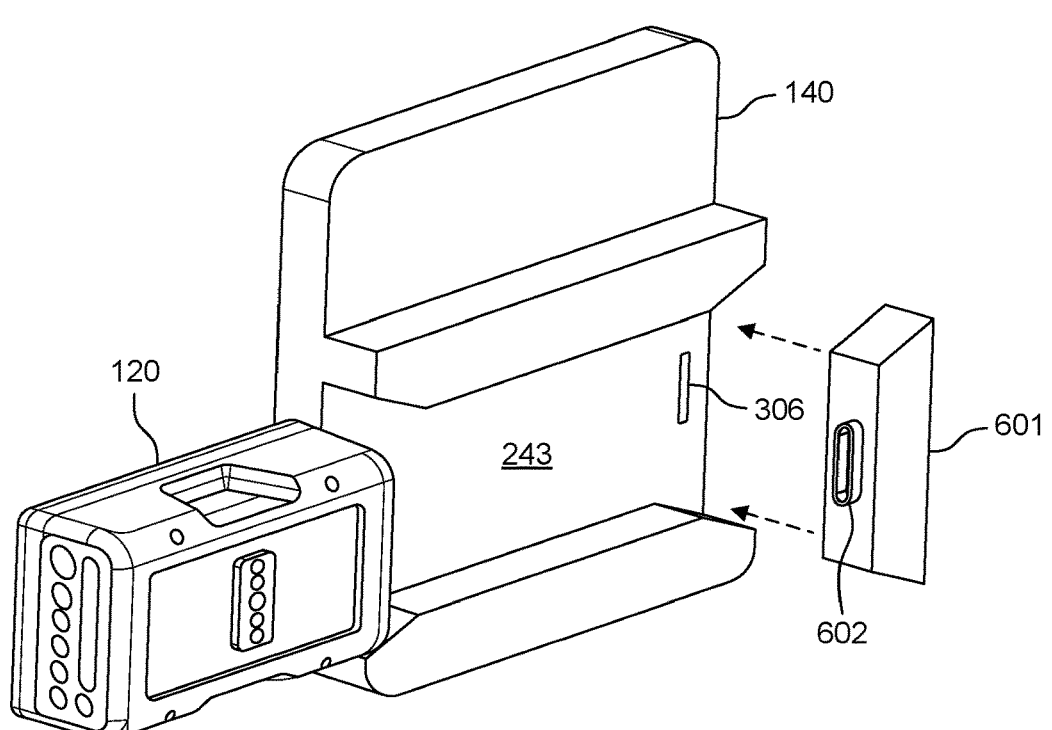
Figure 6C:
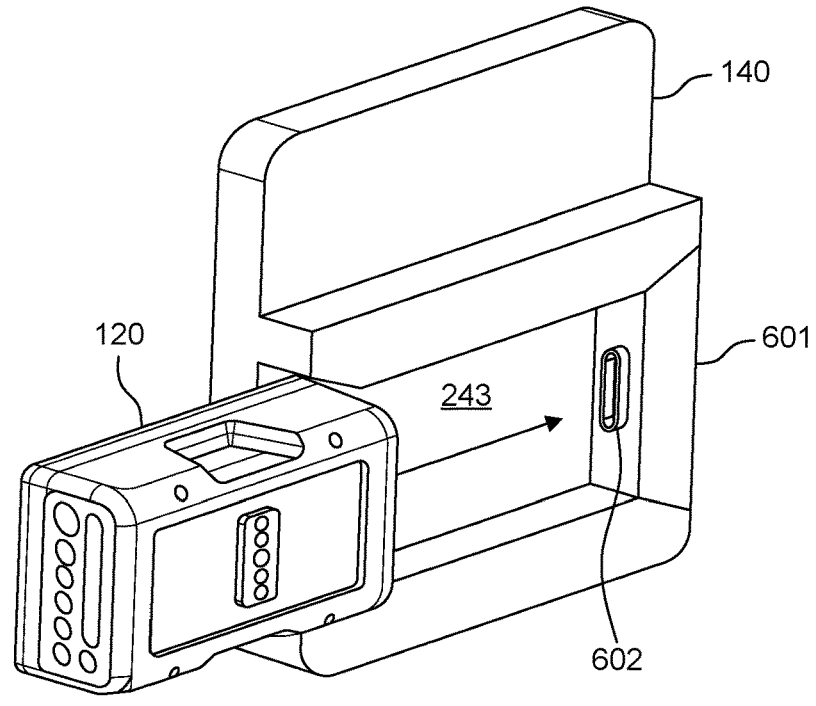
Figure 6D:
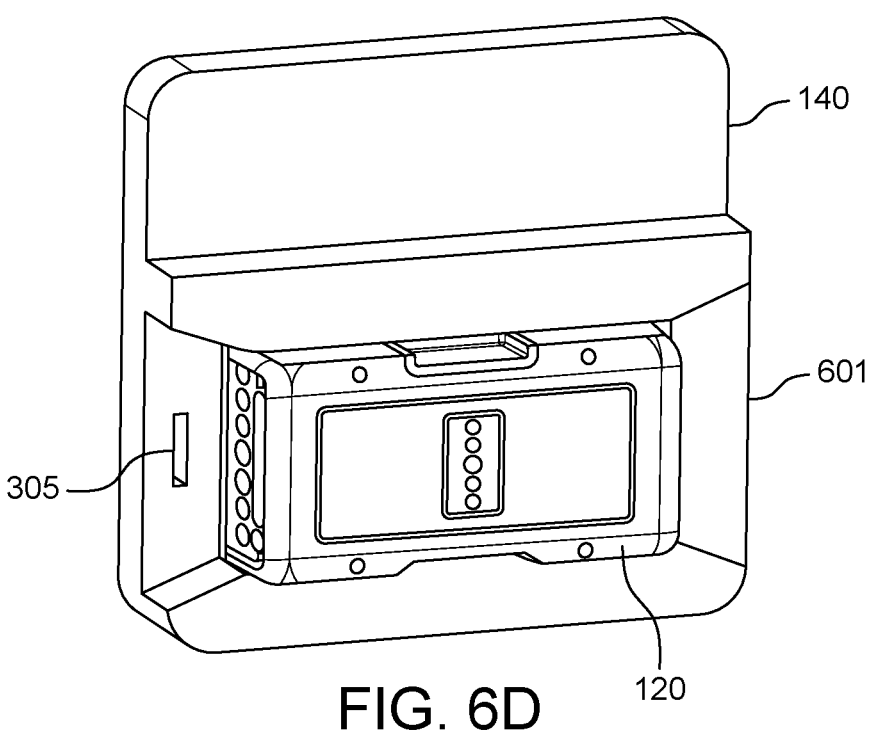
Figure 6E:
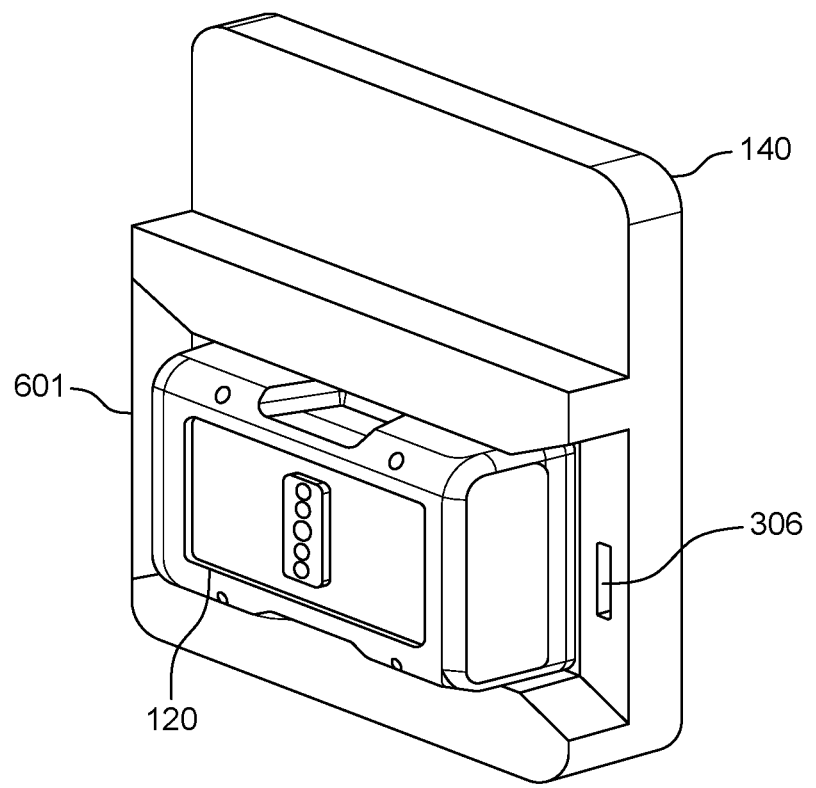

Depending on which lateral direction the docking maneuver is being performed, the electrical interface 603 of the removably interchangeable connector block 601 can be connected to either one of the electrical interfaces 305, 306 of the second monitor 140. For example, if the docking maneuver is being initiated from left-to-right, as shown in FIGS. 6B and 6C, the connector block 601 can be arranged on the right side of the mounting area 243 and connected to electrical interface 306. On the other hand, if the docking maneuver is being initiated from right-to-left, the connector block 601 can be arranged on the left side of the mounting area 243 and connected to electrical interface 305. This modular configuration, again, permits flexibility in mounting to accommodate dynamic patient environments.

Figure 7A:
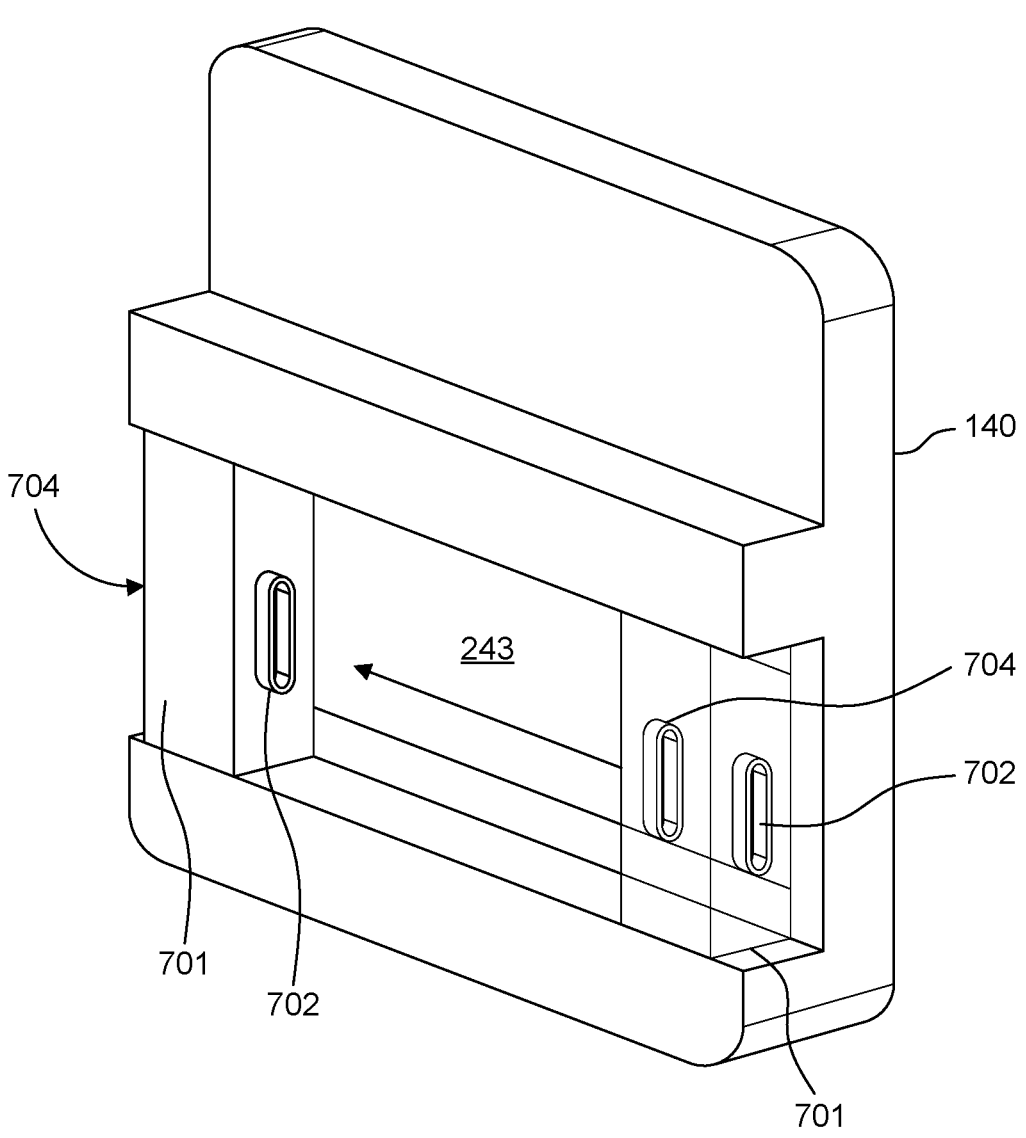
FIGS. 7A-7C are various perspective views of part of the modular system that includes the first monitor and the second monitor and further illustrates a mounting or docking maneuver to mechanically and electrically couple the first monitor and the second monitor together.
Figure 7B:
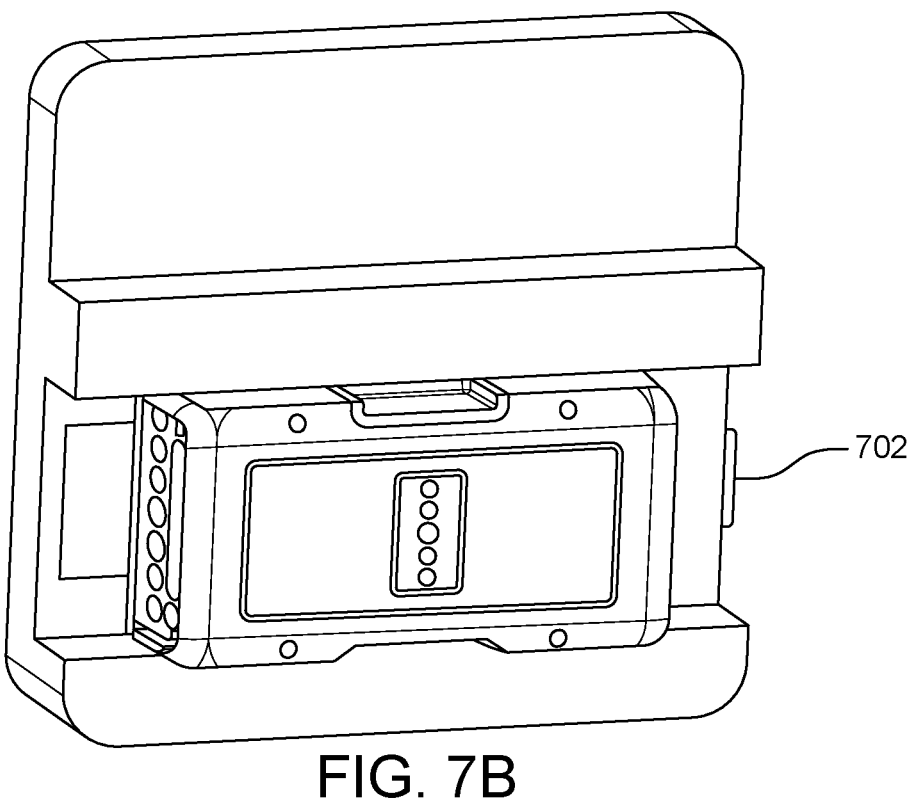
Figure 7C:
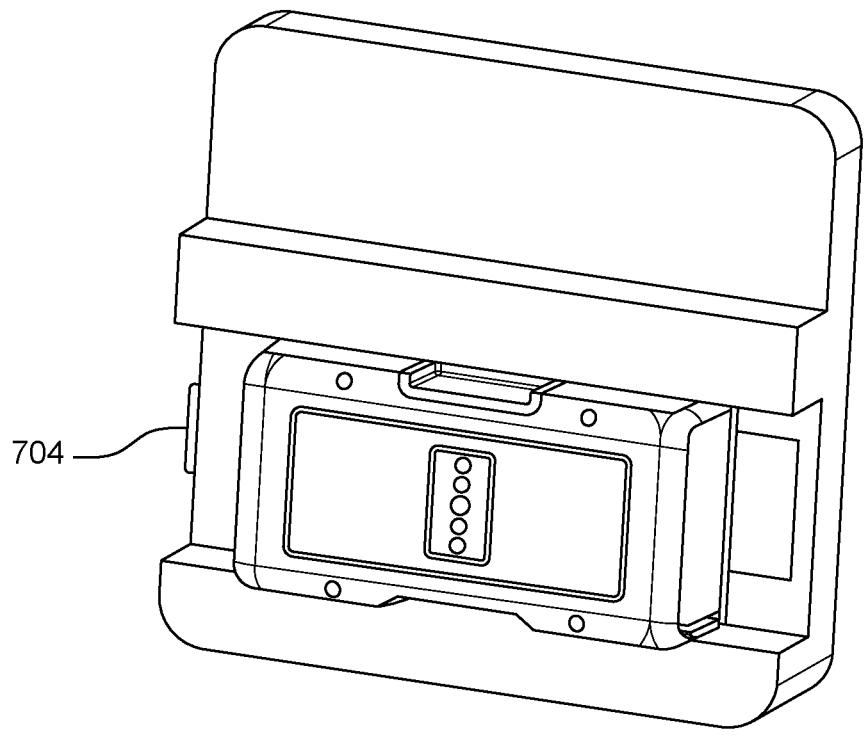

FIGS. 7A-7C are various perspective views of part of the modular system 200 that includes the first monitor 120 and the second monitor 140 and further illustrates a mounting or docking maneuver to mechanically and electrically couple the first monitor 120 and the second monitor 140 together.

The second monitor 140 includes a sliding connector block 701 that is permanently attached to the second monitor 140 within the mounting area 243. The sliding connector block 701 slides on at least one track that extends laterally along the mounting area 243. The sliding connector block 701 includes electrical interfaces 702 and 704 arranged on opposite lateral sides of the connector block 701. The electrical interfaces 702 and 704 are configured to establish an electrical connection to the first monitor 120 with a reciprocal electrical interface of the first monitor (e.g., electrical interface 307). The electrical interfaces 702 and 704 enable the of transfer data signals and power signals between the monitors 120 and 140 in a manner consistent with this disclosure.

The sliding connector block 701 is configured to slide from one lateral side of the mounting area 243 to the other lateral side as it is pushed via the insertion of the first monitor 120 into the mounting area 243. This modular configuration, again, permits flexibility in mounting to accommodate dynamic patient environments.

Figure 8A:
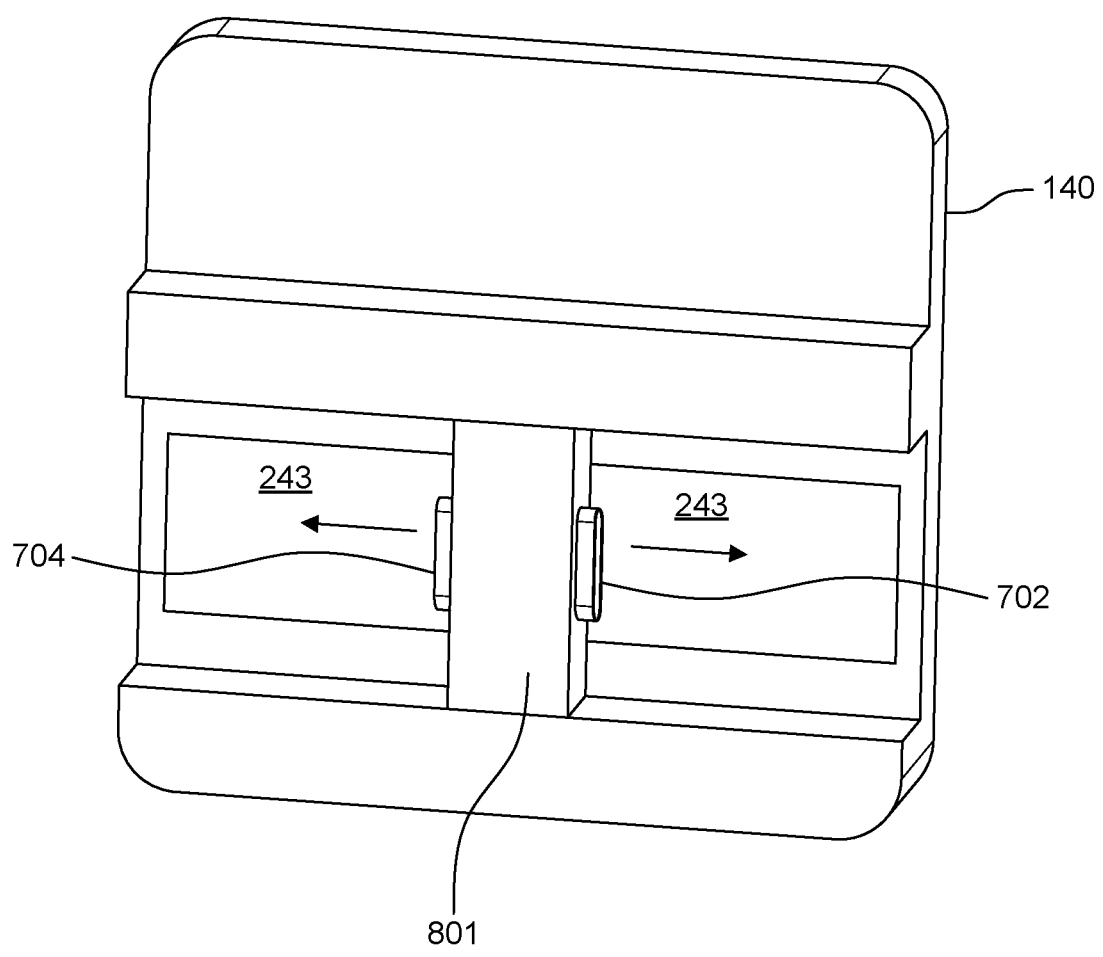
FIGS. 8A-8C are various perspective views of part of the modular system that includes the first monitor and the second monitor and further illustrates a mounting or docking maneuver to mechanically and electrically couple the first monitor and the second monitor together.
Figure 8B:
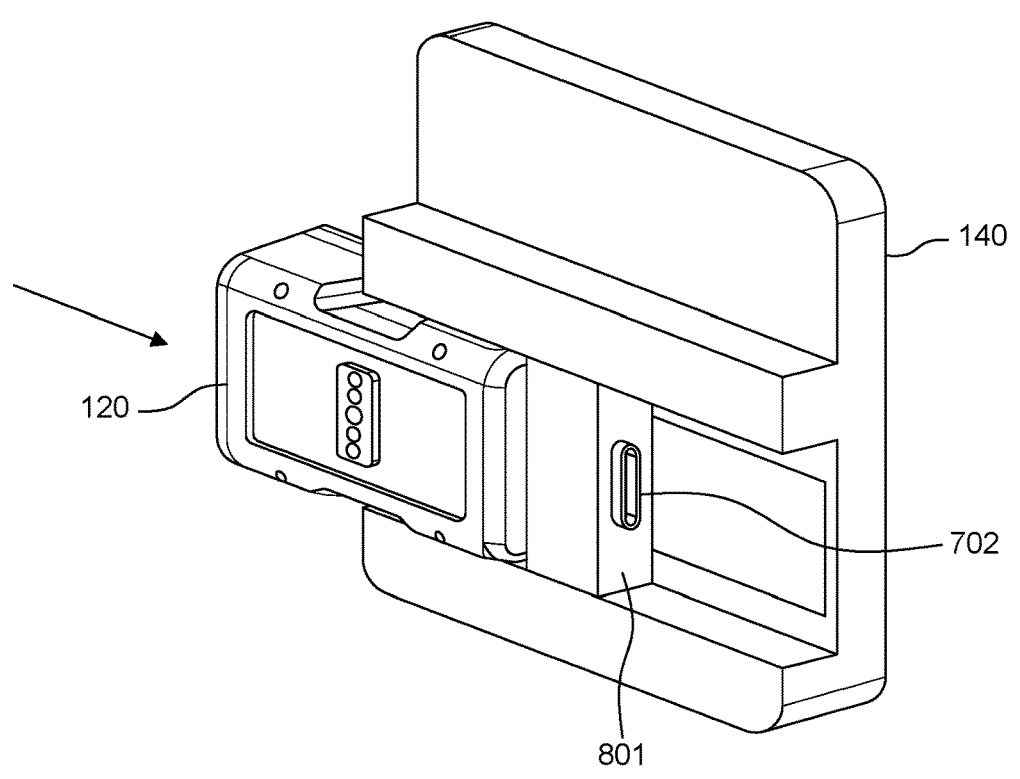
Figure 8C:
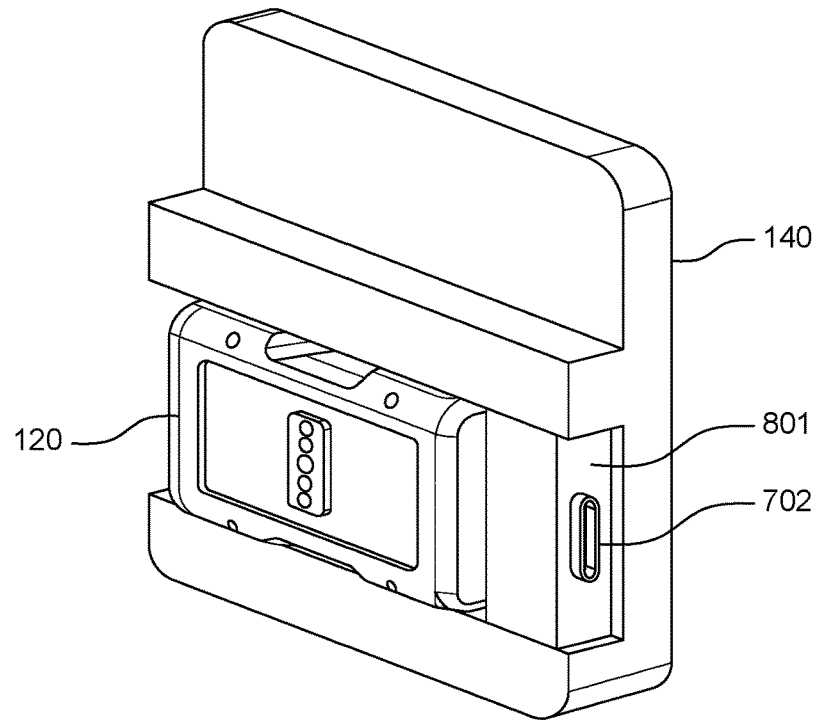

FIGS. 8A-8C are various perspective views of part of the modular system 200 that includes the first monitor 120 and the second monitor 140 and further illustrates a mounting or docking maneuver to mechanically and electrically couple the first monitor 120 and the second monitor 140 together.

The second monitor 140 includes a sliding connector block 801 that is similar to sliding connector block 701 with the exception that it is spring loaded to sit in the center of the mounting area 243 when no counter force is being applied thereto. Like the sliding connector block 701, sliding connector block 801 moves with the first monitor 120 as it is being inserted into or removed from the mounting area 243. Like the sliding connector block 701, sliding connector block 801 includes electrical interfaces 702 and 704 that enable the of transfer data signals and power signals between the monitors 120 and 140 in a manner consistent with this disclosure. This modular configuration, again, permits flexibility in mounting to accommodate dynamic patient environments.

Figure 9B:
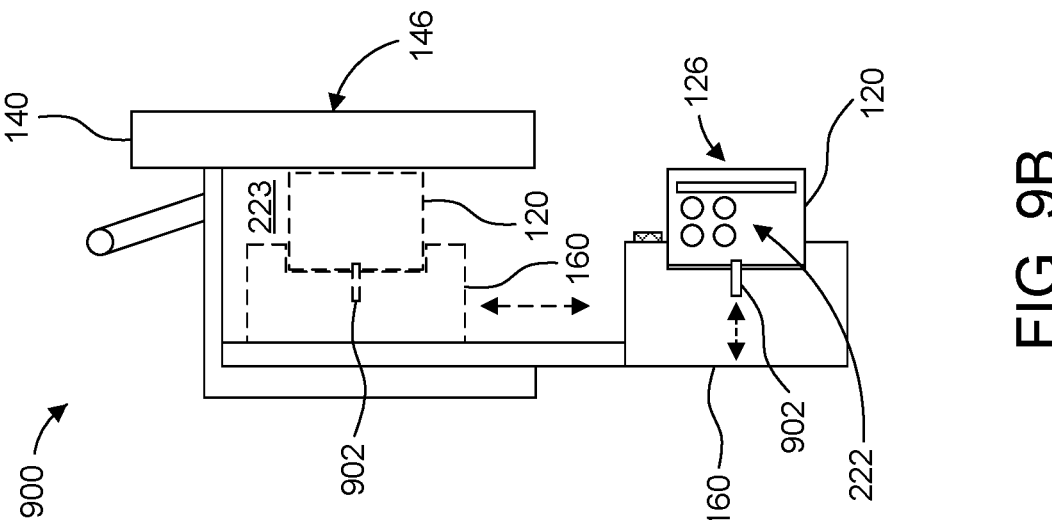
FIGS. 9A and 9B show a front view and a side view, respectively, of a modular system 900 comprising the first monitor, the second monitor, and the monitor mount according to one or more embodiments.
Figure 9A:
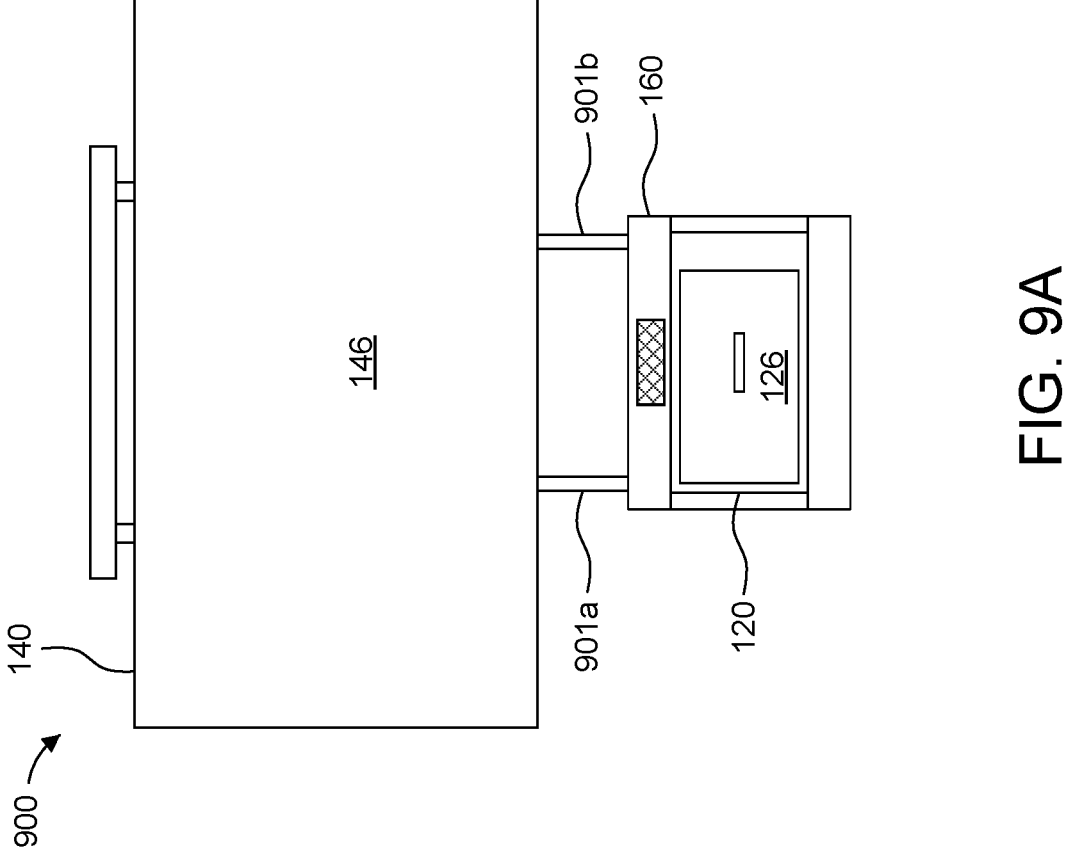

FIGS. 9A and 9B show a front view and a side view, respectively, of a modular system 900 comprising the first monitor 120, the second monitor 140, and the monitor mount 160 according to one or more embodiments. In this case, the second monitor 140 fixed to a retractable monitor mount 160. The monitor mount 160 is mechanically coupled to retractable arms 901, 902 or some other retractable structure, such as a retractable bracket. The retractable arms 901, 902 may be switched between an extended position or a retracted position.

In the extended position, the first monitor 120 and monitor mount 160 hang below the second monitor 140, outside of the mounting area 223. This enables the first monitor 120 to be mounted to the monitor mount 160 or undocked therefrom. It also enables both displays 126 and 146 to actively display information simultaneously, effectively increasing the screen space of the system 900 to increase the amount of information that can be displayed.

In the retracted position, the first monitor 120 and monitor mount 160 are pulled up into the mounting area 223 so that they are both positioned behind the second monitor 140.

The monitor mount 160 further includes an electrical interface 901 that electrically couples to an electrical interface of the first monitor 120 to enable the of transfer data signals and power signals between the first monitor 120 and the monitor mount 160 in a manner consistent with this disclosure. The monitor mount 160 is further configured to transmit data signals from the first monitor 120 to the second monitor 140 so that the second monitor 140 can display information received from the first monitor 120.

Figures 10A, 10B:
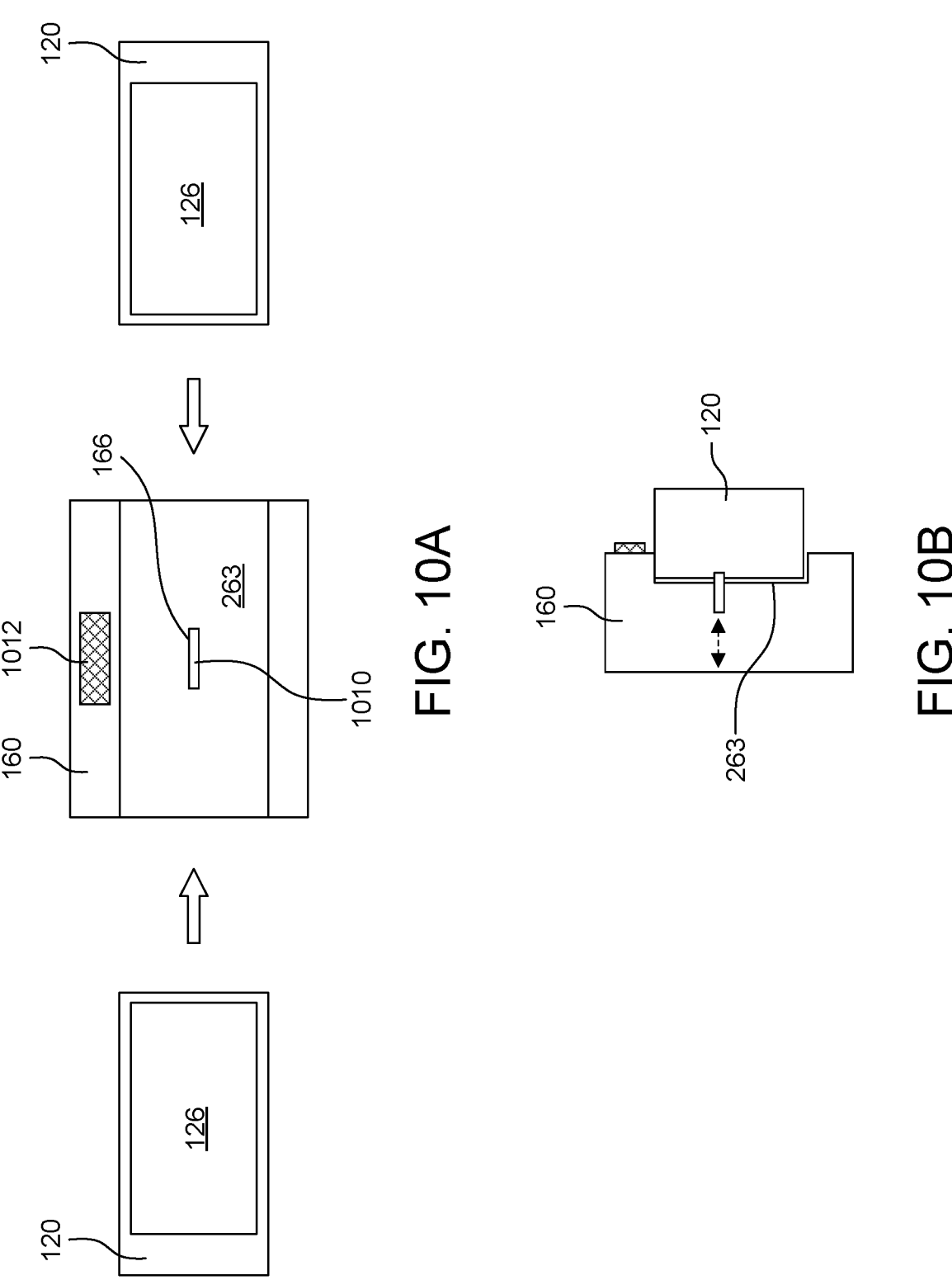
FIGS. 10A and 10B show a front view and a side view, respectively, of a modular system comprising the first monitor and the monitor mount, illustrating a bi-position connector.

FIGS. 10A-B show front and side views of part of the modular system that includes the first monitor 120 and the monitor mount 140. In this arrangement, the first coupling comprises a bi-position connector 1010 is centrally located in the front mounting area 263 of the monitor mount 160. The bi-position connector 1010 is configured to retract into the front mounting area 263 when the first monitor 120 when a release button 1012 is depressed. When the bi-position connector 1010 is retracted, the first monitor 120 can be inserted or removed from front mounting area 263. When the bi-position connector 1010 is extended (see FIG. 10B) it engages and secures the first monitor 120 within the front mounting area 263. The bi-position connector is preferably spring-biased into the extended position. In addition, the communications interface 166 may optionally be integrated into the bi-position connector 1010. The bi-position connector is configured so that it supports making the electrical connections when the monitor is inserted from the left or right. This is done by duplicating the signals in the connector and mirroring the positions of such within the connector. The bi-position connector could optionally incorporate optical signals by placing the optical path in the center of the connector.

Figure 11A:
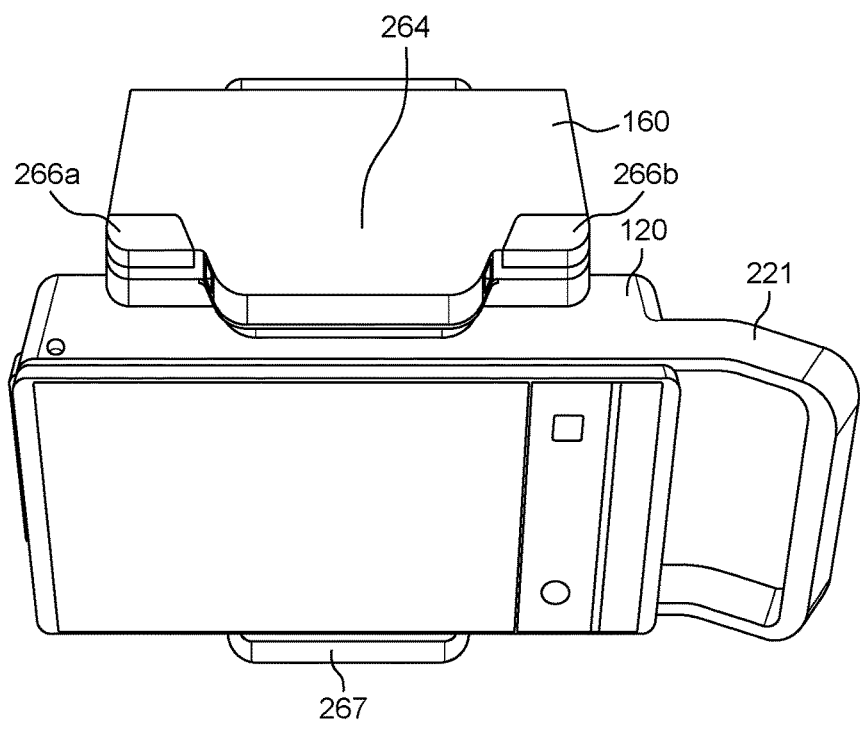
FIGS. 11A and 11B show various perspective views of an alternative arrangement for release levers located on the monitor mount and structure on the second monitor for depressing the release levers when the second monitor is coupled to the monitor mount.
Figure 11B:
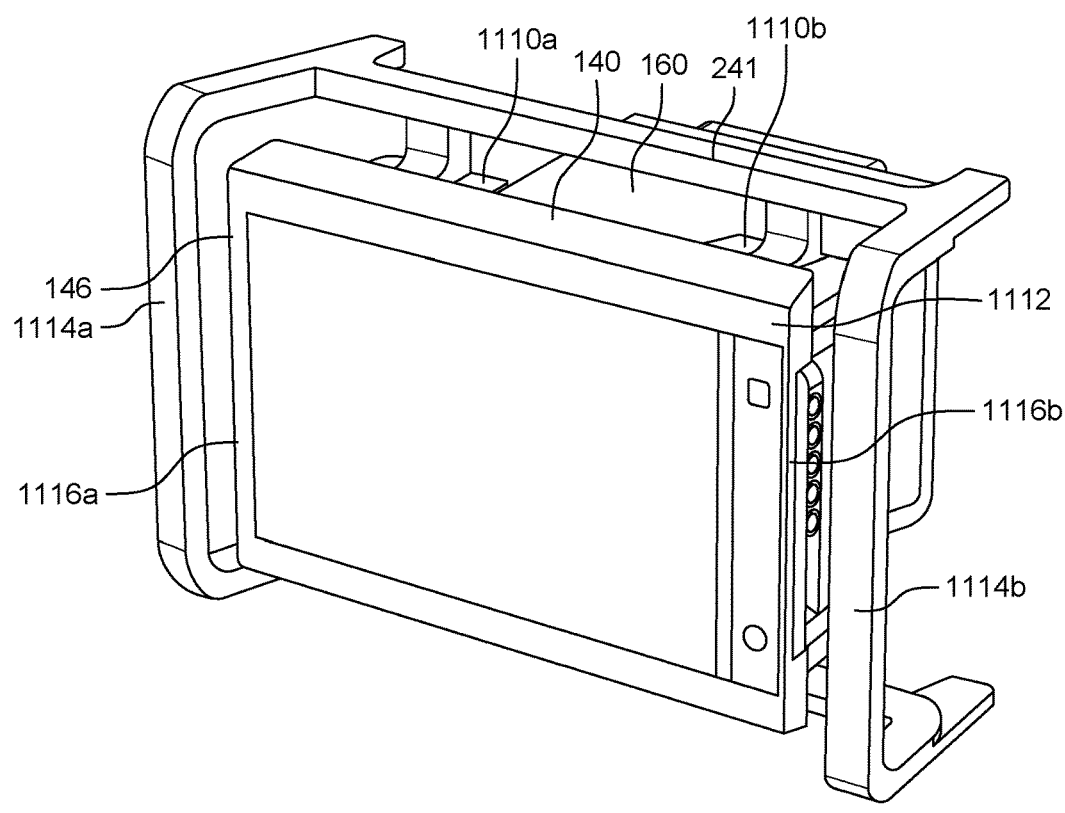

FIGS. 11A-F show various views of additional possible mounting arrangements and structure for the modular system. Referring to FIG. 11A, the first monitor is shown coupled to the monitor mount 160 in a front mounting area defined by upper and lower arms 264, 267. Similar to the arrangements shown in FIGS. 2A-F, the first monitor 120 is released from the coupling mechanism by depressing either one of the release paddles 266a, 266b. In this arrangement the release paddles 266a, 266b vertically overlap (i.e., do not protrude outwardly from) the upper arm 264. This arrangement provides a pleasing visual appearance and additional functionality. When the second monitor 140 is coupled to the monitor mount 160 (see FIG. 11B) latch engaging protrusions 1110a, 1110b that extend from the rear-facing side of the second monitor 120 engage and depress the release paddles 266a, 266b. This functionality enables the first monitor 120 to be coupled to and decoupled from the second monitor 140 while the second monitor 140 is coupled to the monitor mount 160 without the user having the activate a release on the monitor mount 160.

In this arrangement, the second monitor 140 includes a handle 241 that extends around, and is spaced apart from, the perimeter of a housing 1112 in which the electronic visual display 146 and the rear mounting area 243 (see FIG. 2A—not visible in FIG. 11B) are contained. The handle 241 preferably has a bottom surface that is configured to enable the second monitor 140 to remain upright and stable when placed on a horizontal surface, such as a table top. The handle 241 also preferably includes left and right side grip portions 1114a, 1114b that extend substantially parallel to, and are spaced apart from, left and right sides 1116a, 1116b, respectively. In addition, the left and right side grip portions 1114a, 1114b preferably protrude forward beyond the electronic visual display 146. This arrangement protects the electronic visual display 146 from being damaged from objects that may impact the front of the second monitor 140 or if the second monitor is inadvertently dropped.

Figure 11C:
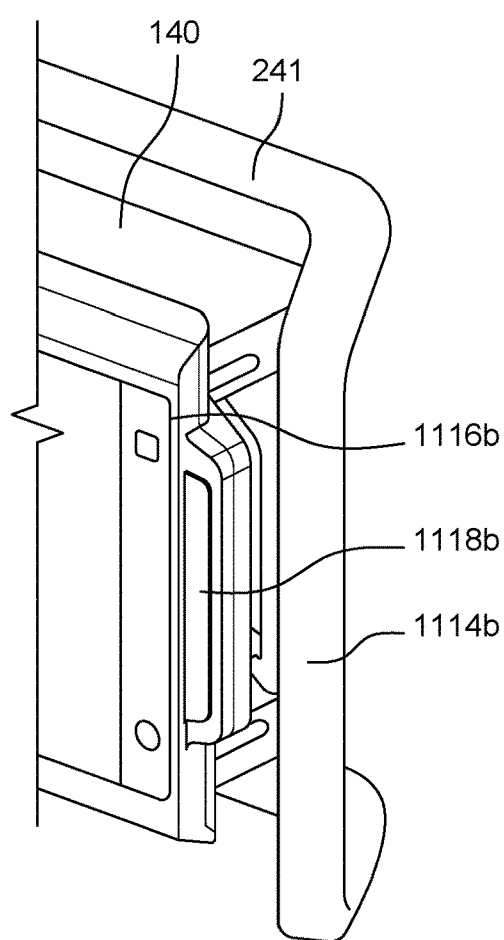
FIGS. 11C and 11D show various perspective views of a handle for the second monitor and release levers for releasing the second monitor from the monitor mount.
Figure 11D:
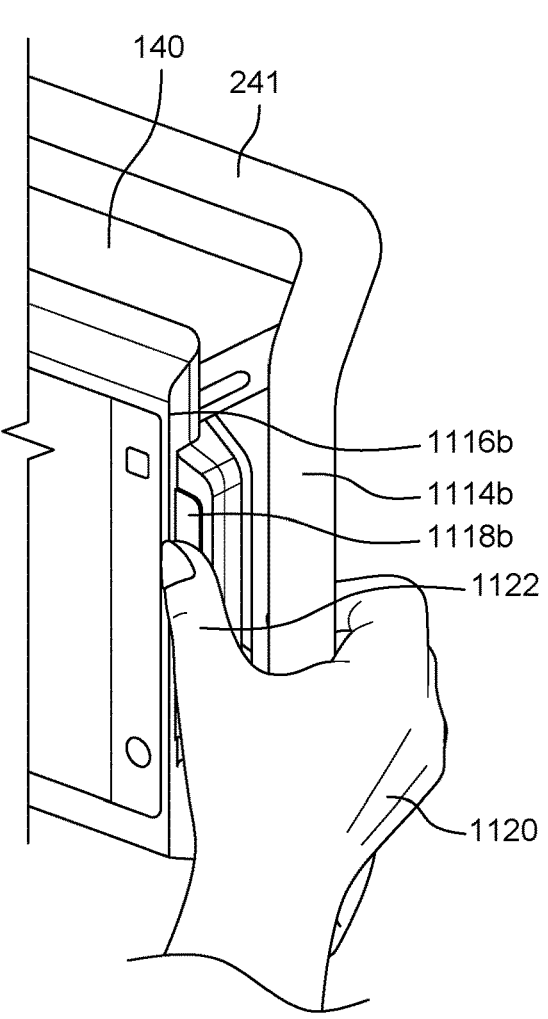

FIGS. 11C-D show a right half of the second monitor 140. It should be understood that the structures described in relation to FIGS. 11C-D have identical structure in a mirror image arrangement on the left half of the second monitor 140. Referring to FIGS. 11C-D, the second monitor 140 includes a pairs of release levers 1118b that are configured to, when simultaneously depressed, disengage the coupling mechanism that detachably secures the second monitor 140 to the monitor mount 160. The release levers 1118b are located along the left and right sides 1116b of the housing 1112. As shown in FIG. 11D, the location and the spacing between the right release lever 1118b and the right side grip portion 1114b of the handle 241 enables the release lever 1118b to be depressed by the thumb 1122 of a user's hand 1120 while the right side grip portion 1114b is being gripped by the user's hand 1120. This configuration is advantageous because it enables the second monitor 140 to be firmly grasped by a user when be decoupled from the monitor mount 160, thereby reducing the risk of accidentally dropping the second monitor 140.

Figures 11E, 11F:
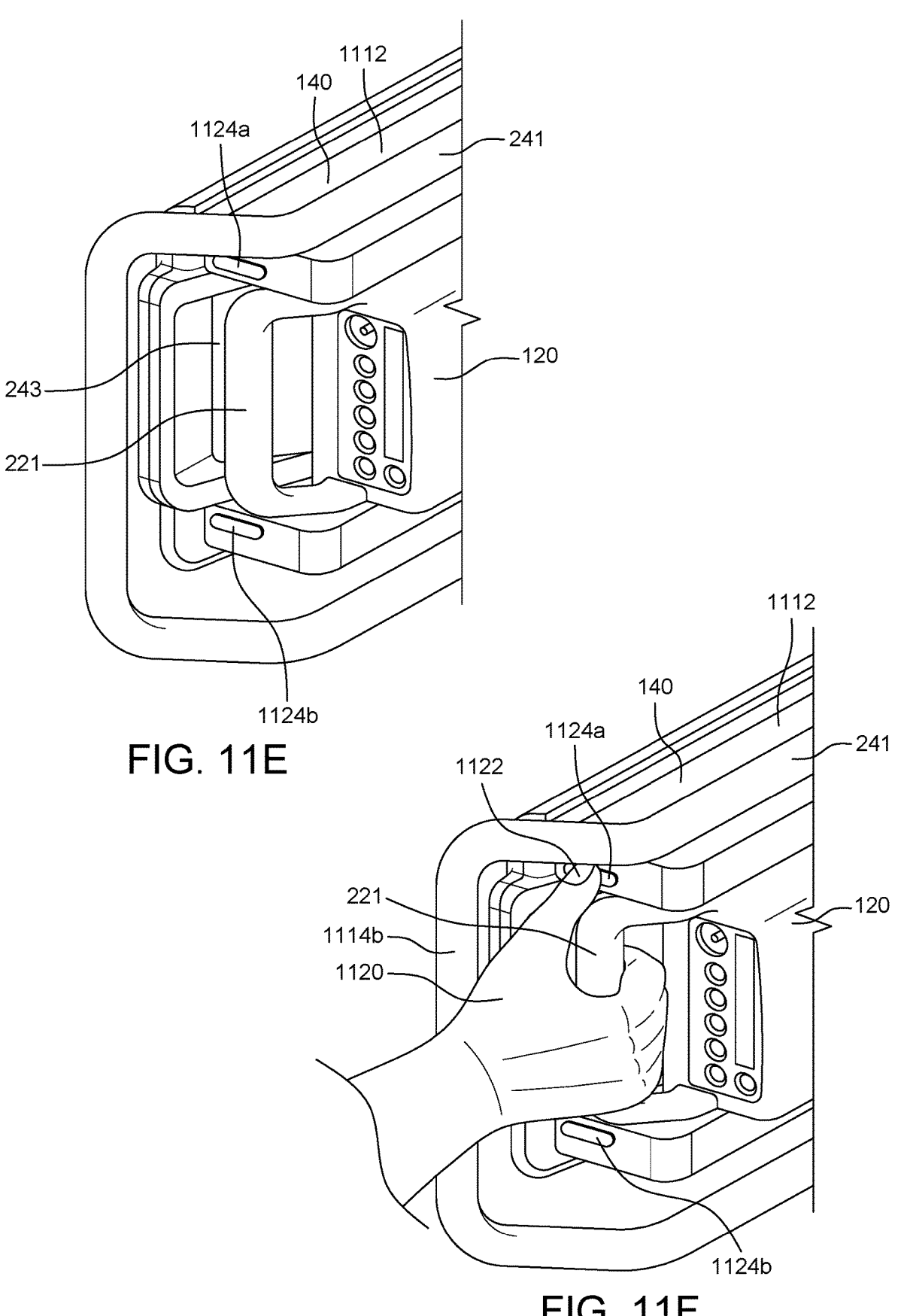
FIGS. 11E and 11F show various perspective views of release levers for releasing the first monitor from the second monitor.

Referring to FIGS. 11E-F, the second monitor 140 also includes two release levers 1124a, 1124b, each of which is configured to independently release the first monitor 120 from the rear mounting area 243, enabling the first monitor 120 to be decoupled from the second monitor 140. One of the release levers 1124a is preferable located on the housing 1112 above the handle 221 of the first monitor 120 when the first monitor 120 is coupled to the second monitor 140 (i.e., fully inserted into the rear mounting area 243). The other release lever 1124b is preferably located on the housing 1112 below the handle 221 of the first monitor 120 when the first monitor 120 is coupled to the second monitor 140. This location of the two release levers 1124a, 1124b enables a user to depress the release lever 1124a, 1124b with the user's thumb 1122 while the handle 221 is being gripped by the user's hand 1120. The direction in which the release levers 1124a, 1126b are depressed is opposite the direction of removal of the first monitor 120, enabling the thumb 1122 to be leveraged to extract the first monitor 120 far enough to become disengaged from the coupling mechanism. Providing levers 1124*a*, 1124*b* both above and below the handle 221 enables the user to release and remove the first monitor 120 using either hand.

Additional mounting arrangements include a guide rail in the rear mounting area 243 having an outer portion that retracts when the first monitor is being inserted into the rear mounting area. The outer portion is the portion of the guide rail that is closest to the end of the rear mounting are in which the first monitor 120 is inserted and removed. This feature allows for a greater amount of misalignment between the first monitor 120 and the rear mounting area 243 as the first monitor 120 is being inserted. As the first monitor 120 is further inserted, the upper and lower walls of the rear mounting area guide the first monitor 120 into more precise alignment. Retraction of the portion of the guide rail could be enabled by separating the outer portion from the rest of the guide rail. Alternatively, the guide rail could pivot about an end that is distal to the outer portion. Preferably, retraction of the outer portion is linked to the release lever(s) that enable the first monitor 120 to be disengaged from the second monitor 140.

A module (not shown) can provide one or more different functions used in delivering healthcare to a patient. The module can acquire patient data including the monitored parameters allocated to a given patient from a network and collate the information for storage in a database. The module can be any of a patient monitoring module for acquiring and processing data generated by at least one physiological sensor monitoring a physiological parameter of a patient (e.g., gas measurement, end-tidal carbon dioxide (etCO2), near-infrared spectroscopy, patient gas, thermoregulation, blood pressure, heart related measurement, pulse oximetry, respiration, neonatal measurement, ventilation, anesthesia information, incubation information, etc.), a patient treatment module for delivering treatment to the patient (e.g., monitoring fluids administered to the patient and supplying anesthesia to the patient, respectively), a control module, a charging module, a compartment module, a converter module, a transmitter module, a relay module, a battery module, a camera module, a purge module, a robot module, an internal and/or external communication module, a power supply module, a global positioning system (GPS) module, a mobile and/or stationary data transfer module, an output board, a facility module, an output board, a dock module, an adapter module, a passive treatment module, an active treatment module, etc.

A processor can process signals derived from the module. In the embodiment depicted in FIG. 1, a processor 162 in a monitor mount 160, a processor 124 in a (first) monitor 120 and/or a processor 142 in another (second) monitor 140 can process signals derived from the module. The monitor mount 160, and the monitors 120, 140 communication interface provide bidirectional communication between the corresponding processor and the module via a network.

Although various embodiments have been described above, these are to be regarded as merely examples. Accordingly, those of ordinary skill in the art will recognize that various changes and modifications of the examples described herein can be made without departing from the spirit and scope of the present disclosure. For example, any feature of any particular portion, embodiment or modification of the monitors 120, 140 may be included or omitted from any of the other portions, embodiments or modifications of the monitors 120, 140. Any feature of any particular portion, embodiment or modification of the monitor mount

160 may be included or omitted from any of the other portions, embodiments or modifications of the monitor mount 160.

Further, it is noted that the present disclosure may be implemented as any combination of a system, an integrated circuit, and a computer program on a non-transitory computer readable recording medium. The processor and any other parts of the computing system may be implemented as Integrated Circuits (IC), Application-Specific Integrated Circuits (ASIC), or Large Scale Integrated circuits (LSI), system LSI, super LSI, or ultra LSI components which perform a part or all of the functions of the computing system.

Each of the parts of the present disclosure can be implemented using many single-function components, or can be one component integrated using the technologies described above. The circuits may also be implemented as a specifically programmed general purpose processor, CPU, a specialized microprocessor such as Digital Signal Processor that can be directed by program instructions on a memory, a Field Programmable Gate Array (FPGA) that can be programmed after manufacturing, or a reconfigurable processor. Some or all of the functions may be implemented by such a processor while some or all of the functions may be implemented by circuitry in any of the forms discussed above.

The present disclosure may be implemented as a non-transitory computer-readable recording medium having recorded thereon a program embodying methods/algorithms for instructing the processor to perform the methods/algorithms. The non-transitory computer-readable recording medium can be, for example, a CD-ROM, DVD, Blu-ray disc, or an electronic memory device.

Each of the elements of the present disclosure may be configured by implementing dedicated hardware or a software program on a memory controlling a processor to perform the functions of any of the components or combinations thereof. Any of the components may be implemented as a CPU or other processor reading and executing a software program from a recording medium such as a hard disk or a semiconductor memory.

It is also contemplated that the implementation of the components of the present disclosure can be done with any newly arising technology that may replace any of the above implementation technologies.

The system of the present disclosure is a modular system providing a universal and scalable platform including a monitor mount capable of mixed use with monitors having different sizes. Traditionally, each type of patient monitor typically required a dedicated monitor mount, a dedicated controller, and a dedicated user interface. Accordingly, traditional monitors of different sizes are not interoperable and the performance advantages of each type of monitor cannot be combined and leveraged. However, since the system of the present disclosure enables the mounting of two monitors having different sizes, shapes, and functionality on a single monitor mount, the two monitors are interoperable with the same controller and the same user interface, and can be universally docked to the monitor mount.

The invention claimed is:

1. A system, comprising:
   a monitor mount including a first mounting area comprising a support portion, a first electrical interface, and a first coupling mechanism, the first coupling mechanism having at least one release paddle;
   a first monitor including a first electronic visual display on a first front-facing portion, a second electrical interface on a first back-facing portion, a third electrical interface on a first end-facing portion, at least one connector port on a second end-facing portion that is distal to the first end-facing portion; and a second monitor including a housing, a second electronic visual display on a second front-facing portion, a second back-facing portion, a second coupling mechanism, the second coupling mechanism having at least one release lever on a side of the housing, and a fourth electrical interface, the second back-facing portion having a second mounting area;

wherein:

the first monitor is detachably couplable to the first mounting area of the monitor mount via the first coupling mechanism, and electronically connected to the monitor mount via the first and second electrical interfaces and wherein the first monitor has a first mounting position and a second mounting position, the first mounting position being 180 degrees offset from the the second mounting position;

the second monitor is detachably couplable to the support portion of the monitor mount, via the second coupling mechanism;

the second monitor further comprises at least one latch engaging protrusion extending from the second back-facing portion, wherein the at least one latch engaging protrusion engages with the at least one release paddle when the second monitor is coupled to the monitor mount; and when the second monitor is coupled to the monitor mount, the first monitor is detachably coupled to the second monitor;

the first monitor and the monitor mount provide an electrical connection between the third electrical interface and the fourth electrical interface when the first monitor is coupled to the second monitor; and the first, second, and third electrical interfaces transmit electrical power when the first monitor is coupled to the second monitor.

2. The system of claim 1 wherein the first mounting area comprises an upper arm and a lower arm connected by a back wall, the upper arm and the lower arm each comprising a portion of the first coupling mechanism.

3. The system of claim 2 wherein the second monitor and the monitor mount are configured to cause the second monitor to engage both the first upper and lower arm when coupled to the monitor mount.

4. The system of claim 2, wherein the at least one release paddle is disposed on at least one of the upper arm and the lower arm, wherein the at least one release paddle does not protrude outward from the upper arm or lower arm.

5. The system of claim 4, further comprising at least one second release paddle, and wherein the at least one release paddle and the at least one second release paddle are disposed on distal edges of the upper arm.

6. The system of claim 1, further comprising a second release lever disposed on an opposite side of the housing from the at least one release lever.

7. The system of claim 1, wherein when the first monitor is detachably coupled to the second monitor the first monitor is disposed within the second mounting area from a first lateral direction through a first side of the second monitor.

8. The system of claim 7, wherein the second monitor further comprises a first monitor release lever located within the housing, wherein when the first monitor release lever is engaged the first monitor decouples from the second monitor.

9. The system of claim 8, further comprising a second monitor release lever located within the housing of the second monitor.

10. The system of claim 9, wherein the first and second monitor release levers are located near the second mounting area at opposite ends of the second mounting area.

11. The system of claim 1 wherein the first monitor includes an end handle, the first monitor being configured so that the end handle protrudes outwardly from the second mounting area when the first monitor is coupled to the second monitor.

12. The system of claim 1, wherein the second monitor is decoupled from the monitor mount when the at least one release lever on the side of the housing is depressed.

13. The system of claim 12, wherein the second monitor decouples from the monitor mount in a release direction and when the at least one release lever on the side of the housing is depressed and wherein the at least one release lever on the side of the housing is depressed in a direction opposite the release direction.

14. The system of claim 1, wherein the second monitor further comprises a handle assembly, the handle assembly having a plurality of grip portions located outboard and spaced apart from the housing and at least one connection member configured to connect the at least one grip portion to the housing.

15. The system of claim 14, wherein the housing comprises a left side and right side located opposite the left side and the plurality of grip portions include a left side grip portion adjacent to the right side and a right side grip portion adjacent to the right side.

16. The system of claim 14, wherein the at least one release lever is located between the second electronic visual display and the second mounting area.

17. A system, comprising:

a monitor mount including a first mounting area, a support portion, a first electrical interface, and a first coupling mechanism, the first coupling mechanism having at least one release paddle;

a first monitor including, a first electronic visual display on a first front-facing portion, a second electrical interface on a first back-facing portion, a third electrical interface on a first end-facing portion, at least one connector port on a second end-facing portion that is distal to the first-end-facing portion; and a second monitor including a second electronic visual display on a second front-facing portion, a second back-facing portion, a fourth electrical interface, the second back-facing portion having a second mounting area, and a housing, wherein the housing defines at least one recess that extends into the housing from a first end of the housing, a second coupling mechanism with at least one release lever on a side of the housing, and a latch engaging protrusion configured to cooperatively engage with the at least one release paddle;

wherein:

the first monitor is detachably couplable to the first mounting area of the monitor mount via the first coupling mechanism and wherein the first monitor is electronically connected to the monitor mount via the first and second electrical interfaces;

the second monitor is detachably couplable to the support portion of the monitor mount via the second coupling mechanism;

wherein the first monitor is detachably couplable to the second monitor via a third coupling mechanism within the second mounting area when the first monitor is inserted into the second mounting area from a first lateral direction or a second lateral direction that is opposite the first lateral direction;

the first monitor is electronically connected to the second monitor via the third electrical interface and the fourth electrical interface when the first monitor is coupled to the second monitor;

the first, second, and third electrical interfaces are each configured to transmit electrical power; and each of the first back-facing portion of the first monitor and the second back portion of the second monitor is configured to be detachably secured to the monitor mount.

18. The system of claim 17, wherein the second monitor further comprises at least a second recess extending into the housing, the second recess located at an opposite end of the housing than the first recess, a first pivoting connector located at a first end of the second mounting area, a second pivoting connector located at second end of the second mounting area, and a fifth electrical interface, the first end being distal to the second end, the fourth electrical interface being located on the first pivoting connecter, the fifth electrical interface being located on the second pivoting connector; and wherein the second pivoting connector is configured to pivot into the housing within the second recess when the first monitor is inserted into the second mounting area from the first lateral direction and the first pivoting connector is configured to pivot into the housing within the first recess when the first monitor is inserted into the second mounting area from the second lateral direction;

wherein the second pivoting connector, the fifth electrical interface, and the first monitor are configured to enable the third electrical interface to connect to the fifth electrical interface when the first monitor is inserted into the second mounting area from the first lateral direction;

wherein the first pivoting connector, the fourth electrical interface, and the first monitor are configured to enable the third electrical interface to connect to the fourth electrical interface when the first monitor is inserted into the second mounting area from the second lateral direction.

19. The system of claim 17, wherein the second coupling comprises at least one rotatable clamp, each of the at least one rotatable clamp being located in the second mounting area and being configured to rotate into a locked position when the first monitor is inserted into the second mounting area and to rotate into an unlocked position when the first monitor is withdrawn from the second mounting area.

20. The system of claim 17, wherein the second monitor further comprises a movable connector block, the fourth electrical interface being positioned in the movable connector block, the movable connector block being positionable at a first end of the second mounting area and a second end of the second mounting area.

* * * * *